(12) United States Patent
Jaccard et al.

(10) Patent No.: US 8,163,479 B2
(45) Date of Patent: Apr. 24, 2012

(54) SPECIFIC SUBSTRATES FOR O$^6$-ALKYLGUANINE-DNA ALKYLTRANSFERASE

(75) Inventors: Hughes Jaccard, Yverdon-les-Bains (CH); Kai Johnsson, Lausanne (CH); Maik Kindermann, Frankfurt (DE); India Christina Sielaff, Lausanne (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 1256 days.

(21) Appl. No.: 10/591,162

(22) PCT Filed: Mar. 1, 2005

(86) PCT No.: PCT/EP2005/050900
§ 371 (c)(1),
(2), (4) Date: Oct. 3, 2006

(87) PCT Pub. No.: WO2005/085470
PCT Pub. Date: Sep. 15, 2005

(65) Prior Publication Data
US 2007/0243568 A1   Oct. 18, 2007

(30) Foreign Application Priority Data
Mar. 2, 2004  (EP) .................................. 04405124

(51) Int. Cl.
*C07D 473/18*  (2006.01)
*C07D 519/00*  (2006.01)
*C07D 495/04*  (2006.01)
*C07D 473/40*  (2006.01)

(52) U.S. Cl. ........... 435/6.1; 435/7.1; 435/7.5; 544/265; 544/269; 544/270; 544/271; 544/272; 544/276; 536/27.81; 548/304.1

(58) Field of Classification Search .................. 544/265, 544/269, 270, 271, 272, 276; 536/27.81
See application file for complete search history.

(56) References Cited

U.S. PATENT DOCUMENTS

| 5,691,307 A | 11/1997 | Moschel et al. |
| 2010/0105053 A1* | 4/2010 | Cho et al. .................... 435/6 |

FOREIGN PATENT DOCUMENTS

| DE | 199 03 895 | 8/2000 |
| WO | 97/20843 | 6/1997 |
| WO | 01/85221 | 11/2001 |
| WO | 02/083937 | 10/2002 |
| WO | 2004/031405 | 4/2004 |

OTHER PUBLICATIONS

Noell, C. Journal of Medicinal & Pharmaceutical Chemistry(1962), 5, 558-88.*
Zheng, Journal of Labelled Compounds & Radiopharmaceuticals (2002), 45(14), 1239-1252.*
Baer, Journal of Pharmacology and Experimental Therapeutics (1984), 229(2), 564-70.*
Vaidyanathan et al., Bioconjugate Chem. 2000, 17, 868-875.*
Baker et al., Journal of Medicinal Chemistry (1968), 11(4), 652-5.*
Damoiseaux, et al., ChemBioChem vol. 2, Issue 4 , pp. 285-287 (2001).*
Keppler Nature Biotechnology 21, 86-89 (2002) Published online: Dec. 9, 2002.*
Calnan et al, Genes Dev. 1991 5: 201-210.*
A. Juillerat et al., "Directed Evolution of O$^6$-Alkylguanine-DNA Alkyltransferase for Efficient Labeling of Fusion Proteins with Small Molecules In Vivo", Chemistry & Biology, vol. 10, No. 4, pp. 313-317, Apr. 2003.
R. Damoiseaux et al., "Synthesis and Applications of Chemical Probes for Human O$^6$-Alkylguanine-DNA Alkyltransferase", Chembiochem—A European Journal of Chemical Biology, vol. 2, No. 4, pp. 285-287, Apr. 2, 2001.
A. Keppler et al., "A General Method for the Covalent Labeling of Fusion Proteins with Small Molecules In Vivo", Nature Biotechnology, vol. 21, No. 1, pp. 86-89, Jan. 20, 2003.

* cited by examiner

*Primary Examiner* — Mark Berch
(74) *Attorney, Agent, or Firm* — New England Biolabs, Inc; Harriet M. Strimpel

(57) ABSTRACT

The invention relates to substrates for O$^6$-alkylguanine-DNA alkyltransferases (AGT) of formula R$_1$-A-X—CH$_2$—R$_3$—R$_4$-L$_1$, wherein A is a group recognized by AGT as a substrate, X is oxygen or sulfur, R$_1$ is a group —R$_2$-L$_2$ or a group R$_5$, R$_2$ and R$_4$ are, independently of each other, a linker, R$_3$ is an aromatic or a heteroaromatic group, or an optionally substituted unsaturated alkyl, cycloalkyl or heterocyclyl group with the double bond connected to CH$_2$, R$_5$ is arylmethyl or heteroarylmethyl or an optionally substituted cycloalkyl, cycloalkenyl or heterocyclyl group, L$_1$ is a label, a plurality of same or different labels, a bond connecting R$_4$ to A forming a cyclic substrate, or a further group —R$_3$—CH$_2$—X-A-R$_1$, and L$_2$ is a label or a plurality of same or different labels. The invention further relates to methods of transferring a label from these substrates to O$^6$-alkylguanine-DNA alkyltransferases (AGT) and AGT fusion proteins.

22 Claims, 3 Drawing Sheets

```
                          SEQUENCE LISTING

<160> NUMBER OF SEQ ID NOS: 1

<210> SEQ ID NO 1
<211> LENGTH: 9
<212> TYPE: PRT
<213> ORGANISM: Human immune deficiency virus

<400> SEQUENCE: 1

Arg Lys Lys Arg Arg Gln Arg Arg Arg
1               5
```

SPECIFIC SUBSTRATES FOR O[6]-ALKYLGUANINE-DNA ALKYLTRANSFERASE

This application is a U.S. national stage of International Application No. PCT/EP/2005/050900 filed Mar. 1, 2005.

FIELD OF THE INVENTION

The present invention relates to methods of transferring a label from substrates to O[6]-alkylguanine-DNA alkyltransferases (AGT) and O[6]-alkylguanine-DNA alkyltransferase fusion proteins, and to novel specific substrates suitable in such methods.

BACKGROUND OF THE INVENTION

The mutagenic and carcinogenic effects of electrophiles such as N-methyl-N-nitrosourea are mainly due to the O[6]-alkylation of guanine in DNA. To protect themselves against DNA-alkylation, mammals and bacteria possess a protein, O[6]-alkylguanine-DNA alkyltransferase (AGT) which repairs these lesions. AGT transfers the alkyl group from the position O[6] of alkylated guanine and guanine derivatives to the mercapto group of one of its own cysteines, resulting in an irreversibly alkylated AGT. The underlying mechanism is a nucleophilic reaction of the $S_N2$ type which explains why not only methyl groups, but also benzylic groups are easily transferred. As overexpression of AGT in tumour cells is the main reason for resistance to alkylating drugs such as procarbazine, dacarbazine, temozolomide and bis-2-chloroethyl-N-nitrosourea, inhibitors of AGT have been proposed for use as sensitisers in chemotherapy (Pegg et al., Prog Nucleic Acid Res Mol Biol 51:167-223, 1995). U.S. Pat. No. 5,691,307 describes O[6]-benzylguanines carrying various substituents in the benzyl group, and their use for depleting AGT levels in tumor cells and thereby increasing responsiveness to alkylating anti-tumor drugs. Likewise, WO 97/20843 discloses further AGT depleting compounds representing O[6]-benzyl- and O[6]-heteroarylmethyl-pyrimidine derivatives.

DE 199 03 895 discloses an assay for measuring levels of AGT which relies on the reaction between biotinylated O[6]-alkylguanine derivatives and AGT which leads to biotinylation of the AGT. This in turn allows the separation of the AGT on a streptavidin coated plate and its detection, e.g. in an ELISA assay. The assay is suggested for monitoring the level of AGT in tumour tissue and for use in screening for AGT inhibitors.

WO 01/85221 proposes the use of radiolabelled fluoro- or iodo-substituted O[6]-benzyl-guanines for detection of AGT and monitoring the level of AGT.

Damoiseaux et al., ChemBiochem. 4:285-287, 2001, disclose modified O[6]-alkylated guanine derivatives incorporated into oligodeoxyribonucleotides for use as chemical probes for labeling AGT, again to facilitate detecting the levels of this enzyme in cancer cells to aid in research and in chemotherapy.

WO 02/083937 discloses a method for detecting and/or manipulating a protein of interest wherein the protein is fused to AGT and the AGT fusion protein contacted with an AGT substrate carrying a label, and the AGT fusion protein detected and optionally further manipulated using the label. Several AGT fusion proteins to be used, general structural principles of the AGT substrate and a broad variety of labels and methods to detect the label useful in the method are described.

PCT/EP03/10859 (WO 2004/031404) describes particular AGT fusion proteins to be used in the mentioned method for detecting and/or manipulating a protein of interest, labelled fusion proteins obtainable by this method, and the method using the particular AGT fusion proteins.

PCT/EP03/10889 (WO 2004/031405) discloses additional AGT substrates carrying a label particularly suitable in the mentioned method for detecting and/or manipulating a protein of interest, and the application of such particularly labelled substrates. This patent application also describes methods of manufacture of these additional AGT substrates.

SUMMARY OF THE INVENTION

The invention relates to substrates for O[6]-alkylguanine-DNA alkyltransferases (AGT) of formula (1)

$$R_1\text{-A-X}-CH_2-R_3-R_4\text{-}L_1 \tag{1}$$

wherein A is a group recognized by AGT as a substrate;

X is oxygen or sulfur;

$R_1$ is a group $-R_2\text{-}L_2$ or a group $R_5$;

$R_2$ and $R_4$ are, independently of each other, a linker;

$R_3$ is an aromatic or a heteroaromatic group, or an optionally substituted unsaturated alkyl, cycloalkyl or heterocyclyl group with the double bond connected to $CH_2$;

$R_5$ is arylmethyl or heteroarylmethyl or an optionally substituted cycloalkyl, cycloalkenyl or heterocyclyl group;

$L_1$ is a label, a plurality of same or different labels, a bond connecting $R_4$ to A forming a cyclic substrate, or a further group $-R_3-CH_2-X\text{-A-}R_1$; and $L_2$ is a label or a plurality of same or different labels.

The invention further relates to methods of transferring a label from these substrates to O[6]-alkylguanine-DNA alkyltransferases (AGT) and AGT fusion proteins.

DETAILED DESCRIPTION OF THE INVENTION

Figure 1:
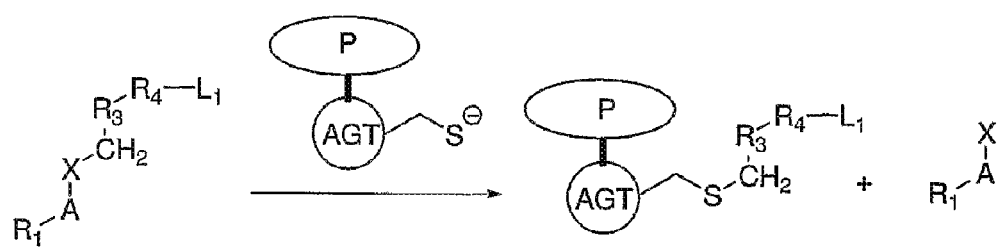
FIG. 1: Schematic representation of the reaction of fusion protein comprising a protein of interest (P) and AGT with substrates of formula .

The particular AGT substrates of the invention are compounds of formula (1)

(1)

wherein A is a group recognized by AGT as a substrate;
X is oxygen or sulfur;
$R_1$ is a group —$R_2$-$L_2$ or a group $R_5$;
$R_2$ and $R_4$ are, independently of each other, a linker;
$R_3$ is an aromatic or a heteroaromatic group, or an optionally substituted unsaturated alkyl, cycloalkyl or heterocyclyl group with the double bond connected to $CH_2$;
$R_5$ is arylmethyl or heteroarylmethyl or an optionally substituted cycloalkyl, cycloalkenyl or heterocyclyl group,
$L_1$ is a label, a plurality of same or different labels, a bond connecting $R_4$ to A forming a cyclic substrate, or a further group —$R_3$—$CH_2$—X-A-$R_1$; and
$L_2$ is a label or a plurality of same or different labels.

In a group $R_1$-A, the residue A is preferably a heteroaromatic group containing 1 to 5 nitrogen atoms, recognized by AGT as a substrate.

A heteroaromatic group A is mono- or bicyclic and has 5 to 12, preferably 6 or 9 or 10 ring atoms; which in addition to carrying a substituent $R_1$ may be unsubstituted or substituted by one or more, especially one, two or three further substituents selected from the group consisting of lower alkyl, such as methyl, lower alkoxy, such as methoxy or ethoxy, hydroxy, oxo, amino, lower alkylamino, di-lower alkylamino, acylamino, halogen, such as chlorine or bromine, halogenated lower alkyl, such as trifluoromethyl, carboxy, lower alkoxycarbonyl, carbamoyl, lower alkylcarbamoyl, or lower alkylcarbonyl.

Lower alkyl is preferably alkyl with 1 to 7, preferably from 1 to 4 C atoms, and is linear or branched; preferably, lower alkyl is butyl, such as n-butyl, sec-butyl, isobutyl, tert-butyl, propyl, such as n-propyl or isopropyl, ethyl or methyl. Most preferably, lower alkyl is methyl.

In lower alkoxy, the lower alkyl group is as defined hereinbefore. Lower alkoxy denotes preferably n-butoxy, tert-butoxy, iso-propoxy, ethoxy, or methoxy, in particular methoxy.

Preferably the mono- or bicyclic heteroaromatic group A is selected from 2H-pyrrolyl, pyrrolyl, imidazolyl, benzimidazolyl, pyrazolyl, indazolyl, purinyl, 8-azapurinyl, 7-deazapurinyl, 8-aza-7-deazapurinyl, pyridyl, pyrazinyl, pyrimidinyl, pyridazinyl, triazinyl, 4H-quinolizinyl, isoquinolyl, quinolyl, phthalazinyl, naphthyridinyl, quinoxalyl, quinazolinyl, quinolinyl, pteridinyl, indolizinyl, 3H-indolyl, indolyl, isoindolyl, triazolyl, tetrazolyl, or benzo[d]pyrazolyl. More preferably the mono- or bicyclic heteroaromatic group A is selected from the group consisting of purinyl, 8-azapurinyl, 7-deazapurinyl, 8-aza-7-deazapurinyl, pyridyl, pyrazinyl, pyrimidinyl, pyridazinyl and triazinyl.

For example the group $R_1$-A may be a purine radical of formula (2)

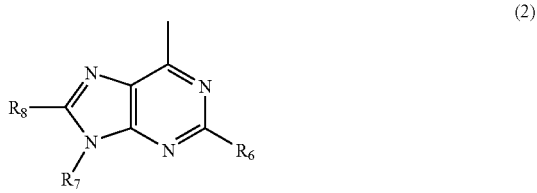
(2)

wherein $R_6$ is hydrogen, hydroxy or unsubstituted or substituted amino; and one of $R_7$ and $R_8$ is $R_1$ and the other one is hydrogen.

If $R_6$ is hydroxy, the purine radical is predominantly present in its tautomeric form wherein a nitrogen adjacent to the carbon atom bearing $R_6$ carries a hydrogen atom, the double bond between this nitrogen atom and the carbon atom bearing $R_6$ is a single bond, and $R_6$ is double bonded oxygen, respectively.

A substituted amino group $R_6$ is lower alkylamino of 1 to 4 carbon atoms or acylamino, wherein the acyl group is lower alkylcarbonyl with 1 to 5 carbon atoms, e.g. acetyl, propionyl, n- or isopropylcarbonyl, or n-, iso- or tert-butylcarbonyl, or arylcarbonyl, e.g. benzoyl.

If $R_6$ is unsubstituted or substituted amino and the residue X connected to the bond of the purine radical is oxygen, the residue of formula (2) is a guanine derivative.

Particularly preferred are compounds wherein the group $R_1$-A is a purine radical of formula (2), $R_6$ is unsubstituted amino, $R_7$ is $R_1$, $R_8$ is hydrogen, and X is oxygen, i.e. a guanine derivative carrying a further substituent in position $N^9$.

In another preferred embodiment of the invention the group $R_1$-A is an 8-azapurine radical of formula (3)

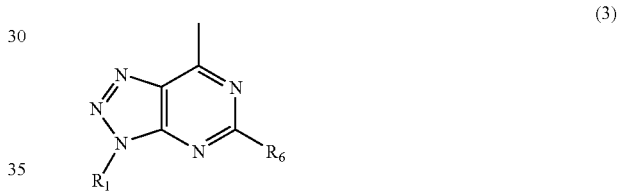
(3)

wherein the substituents $R_6$ has the meaning as defined for $R_6$ under formula (2).

In a further preferred embodiment of the invention the group $R_1$-A is a pyrimidine radical of formula (4a) or (4b)

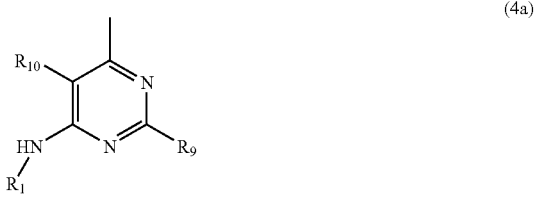
(4a)

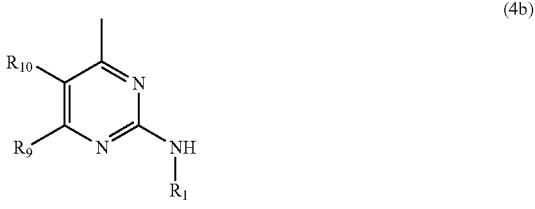
(4b)

wherein $R_9$ is hydrogen, halogen, lower alkyl with 1 to 4 carbon atoms or amino, preferably amino, and $R_{10}$ is hydrogen, halogen, lower alkyl with 1 to 4 carbon atoms, amino, nitro or nitroso. Halogen $R_9$ or $R_{10}$ is e.g. fluoro, chloro, bromo or iodo.

X is preferably oxygen.

In a further preferred embodiment of the invention the group $R_1$-A is a pteridine radical of formula (4c)

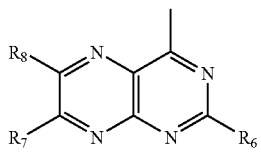

wherein $R_6$ is unsubstituted or substituted amino; and one of $R_7$ and $R_8$ is $R_1$ and the other one is hydrogen.

A linker group $R_2$ or $R_4$ is preferably a flexible linker connecting a label $L_2$ or $L_1$, respectively, or a plurality of same or different labels $L_2$ or $L_1$ to the substrate. Linker units are chosen in the context of the envisioned application, i.e. in the transfer of the substrate to a fusion protein comprising AGT. They also increase the solubility of the substrate in the appropriate solvent. The linkers used are chemically stable under the conditions of the actual application. The linker does not interfere with the reaction with AGT nor with the detection of the label $L_1$ and/or $L_2$, but may be constructed such as to be cleaved at some point in time after the reaction of the compound of formula (1) with the fusion protein comprising AGT.

A linker $R_2$ or $R_4$ is a straight or branched chain alkylene group with 1 to 300 carbon atoms, wherein optionally
(a) one or more carbon atoms are replaced by oxygen, in particular wherein every third carbon atom is replaced by oxygen, e.g. a poylethyleneoxy group with 1 to 100 ethyleneoxy units;
(b) one or more carbon atoms are replaced by nitrogen carrying a hydrogen atom, and the adjacent carbon atoms are substituted by oxo, representing an amide function —NH—CO—;
(c) one or more carbon atoms are replaced by oxygen, and the adjacent carbon atoms are substituted by oxo, representing an ester function —O—CO—;
(d) the bond between two adjacent carbon atoms is a double or a triple bond, representing a function —CH=CH— or —C≡C—;
(e) one or more carbon atoms are replaced by a phenylene, a saturated or unsaturated cycloalkylene, a saturated or unsaturated bicycloalkylene, a bridging heteroaromatic or a bridging saturated or unsaturated heterocyclyl group;
(f) two adjacent carbon atoms are replaced by a disulfide linkage —S—S—; or a combination of two or more, especially two or three, alkylene and/or modified alkylene groups as defined under (a) to (f) hereinbefore, optionally containing substituents.

Substituents considered are e.g. lower alkyl, e.g. methyl, lower alkoxy, e.g. methoxy, lower acyloxy, e.g. acetoxy, or halogenyl, e.g. chloro.

Further substituents considered are e.g. those obtained when an α-amino acid, in particular a naturally occurring α-amino acid, is incorporated in the linker $R_2$ or $R_4$ wherein carbon atoms are replaced by amide functions —NH—CO— as defined under (b). In such a linker, part of the carbon chain of the alkylene group $R_2$ or $R_4$ is replaced by a group —(NH—CHR—CO)$_n$— wherein n is between 1 and 100 and R represents a varying residue of an α-amino acid.

A further substituent is one which leads to a photocleavable linker $R_2$ or $R_4$, e.g. an o-nitrophenyl group. In particular this substituent o-nitrophenyl is located at a carbon atom adjacent to an amide bond, e.g. in a group —NH—CO—CH$_2$—CH(o-nitrophenyl)-NH—CO—, or as a substituent in a polyethylene glycol chain, e.g. in a group —O—CH$_2$—CH(o-nitrophenyl)-O—. Other photocleavable linkers considered are e.g. phenacyl, alkoxybenzoin, benzylthioether and pivaloyl glycol derivatives.

A phenylene group replacing carbon atoms as defined under (e) hereinbefore is e.g. 1,2-, 1,3-, or preferably 1,4-phenylene. In a particular embodiment, the phenylene group is further substituted by a nitro group, and, combined with other replacements as mentioned above under (a), (b), (c), (d), and (f), represents a photocleavable group, and is e.g. 4-nitro-1,3-phenylene, such as in —CO—NH—CH$_2$-4-nitro-1,3-phenylene-CH(CH$_3$)—O—CO—, or 2-methoxy-5-nitro-1,4-phenylene, such as in —CH$_2$—O-2-methoxy-5-nitro-1,4-phenylene-CH(CH$_3$)—O—. Other particular embodiments representing photocleavable linkers are e.g. -1,4-phenylene-CO—CH$_2$—O—CO—CH$_2$— (a phenacyl group), -1,4-phenylene-CH(OR)—CO-1,4-phenylene- (an alkoxybenzoin), or -3,5-dimethoxy-1,4-phenylene-CH$_2$—O— (a dimethoxybenzyl moiety). A saturated or unsaturated cycloalkylene group replacing carbon atoms as defined under (e) hereinbefore is derived from cycloalkyl with 3 to 7 carbon atoms, preferably from cyclopentyl or cyclohexyl, and is e.g. 1,2- or 1,3-cyclopentylene, 1,2-, 1,3-, or preferably 1,4-cyclohexylene, or also 1,4-cyclohexylene being unsaturated e.g. in 1- or in 2-position. A saturated or unsaturated bicycloalkylene group replacing carbon atoms as defined under (e) hereinbefore is derived from bicycloalkyl with 7 or 8 carbon atoms, and is e.g. bicyclo[2.2.1]heptylene or bicyclo[2.2.2]octylene, preferably 1,4-bicyclo[2.2.1]-heptylene optionally unsaturated in 2-position or doubly unsaturated in 2- and 5-position, and 1,4-bicyclo[2.2.2]octylene optionally unsaturated in 2-position or doubly unsaturated in 2- and 5-position. A bridging heteroaromatic group replacing carbon atoms as defined under (e) hereinbefore is e.g. triazolidene, preferably 1,4-triazolidene, or isoxazolidene, preferably 3,5-isoxazolidene. A bridging saturated or unsaturated heterocyclyl group replacing carbon atoms as defined under (e) hereinbefore is e.g. derived from an unsaturated heterocyclyl group as defined under $R_3$ above, e.g. isoxazolidinene, preferably 3,5-isoxazolidinene, or a fully saturated heterocyclyl group with 3 to 12 atoms, 1 to 3 of which are heteroatoms selected from nitrogen, oxygen and sulfur, e.g. pyrrolidinediyl, piperidinediyl, tetrahydrofuranediyl, dioxanediyl, morpholinediyl or tetrahydrothiophenediyl, preferably 2,5-tetrahydrofuranediyl or 2,5-dioxanediyl. A particular heterocyclyl group considered is a saccharide moiety, e.g. an α- or β-furanosyl or α- or β-pyranosyl moiety.

Cyclic substructures in a linker $R_2$ or $R_4$ reduce the molecular flexibility as measured by the number of rotatable bonds within $R_2$ or $R_4$, which leads to a better membrane permeation rate, important for all in vivo labeling applications.

A linker $R_2$ or $R_4$ is preferably a straight chain alkylene group with 1 to 25 carbon atoms or a straight chain polyethylene glycol group with 4 to 100 ethyleneoxy units, optionally attached to the group A or $R_3$, respectively, by a —CH=CH— or —C≡C— group. Further preferred is a straight chain alkylene group with 1 to 25 carbon atoms wherein carbon atoms are optionally replaced by an amide function —NH—CO—, and carrying a photo-cleavable subunit, e.g. o-nitrophenyl. Further preferred are branched linkers comprising a polyethylene glycol group of 3 to 6 ethylene glycol units and alkylene groups wherein carbon atoms are replaced by amide bonds, and further carrying substituted amino and hydroxy functions. Other preferred branched linkers have dendritic (tree-like) structures wherein amine, carboxamide and/or ether functions replace carbon atoms of an alkylene group.

A particularly preferred linker $R_2$ or $R_4$ is a straight chain alkylene group of 10 to 40 carbon atoms wherein 3 to 12 carbon atoms are replaced by oxygen, one or two carbon atoms are replaced by one or two 1,4-triazolidene units, respectively, and optionally one carbon atom is replaced by a 1,4-phenylene unit.

Another particularly preferred linker $R_2$ or $R_4$ is a straight chain alkylene group of 10 to 40 carbon atoms optionally substituted by oxo wherein 3 to 12 carbon atoms are replaced by oxygen and one or two carbon atoms are replaced by nitrogen.

Another particularly preferred linker $R_2$ or $R_4$ is a straight chain alkylene group of 6 to 40 carbon atoms wherein 2 to 12 carbon atoms are replaced by oxygen and one or two bonds between two adjacent carbon atoms is a double bond representing a function —CH=CH—.

Another particularly preferred linker $R_2$ or $R_4$ is a straight chain alkylene group of 1 to 15 carbon atoms, and an N-methylisoxazolidine-3,5-dimethyl group.

A linker $R_2$ or $R_4$ may carry one or more same or different labels, e.g. 1 to 100 same or different labels, in particular 1 to 5, preferably one, two or three, in particular one or two same or different labels.

$R_3$ as an aromatic or a heteroaromatic group, or as an optionally substituted unsaturated alkyl, cycloalkyl or heterocyclyl group is a group sterically and electronically accepted by AGT (in accordance with its reaction mechanism), which allows the covalent transfer of the $R_3$—$R_4$-$L_1$ unit to the fusion protein. In a $R_3$—$R_4$-$L_1$ unit, $R_4$-$L_1$ may also have the meaning of a plurality of same or different linkers $R_4$ carrying a plurality of same or different labels $L_1$.

$R_3$ as an aromatic group is preferably phenyl or naphthyl, in particular phenyl, e.g. phenyl substituted by $R_4$ in para or meta position.

A heteroaromatic group $R_3$ is a mono- or bicyclic heteroaryl group comprising zero, one, two, three or four ring nitrogen atoms and zero or one oxygen atom and zero or one sulfur atom, with the proviso that at least one ring carbon atom is replaced by a nitrogen, oxygen or sulfur atom, and which has 5 to 12, preferably 5 or 6 ring atoms; and which in addition to carrying a substituent $R_4$ may be unsubstituted or substituted by one or more, especially one, further substituents selected from the group consisting of lower alkyl, such as methyl, lower alkoxy, such as methoxy or ethoxy, halogen, e.g. chlorine, bromine or fluorine, halogenated lower alkyl, such as trifluoromethyl, or hydroxy.

Preferably the mono- or bicyclic heteroaryl group $R_3$ is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]-pyrazolyl, thienyl, and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, e.g. 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, triazolyl, tetrazolyl, benzo[d]pyrazolyl, thienyl, and furanyl.

In a particularly preferred embodiment of the invention the heteroaryl group $R_3$ is triazolyl, especially 1-triazolyl, carrying the further substituent $R_4$ in the 4- or 5-position, tetrazolyl, especially 1-tetrazolyl, carrying the further substituent $R_4$ in the 4- or 5-position, or 2-tetrazolyl carrying the further substituent $R_4$ in 5-position, isoxazolyl, especially 3-isoxazolyl carrying the further substituent $R_4$ in 5-position, or 5-isoxazolyl, carrying the further substituent $R_4$ in 3-position, or thienyl, especially 2-thienyl, carrying the further substituent $R_4$ in 3-, 4- or 5-position, preferably 4-position, or 3-thienyl, carrying the further substituent $R_4$ in 4-position.

Most preferred is the heteroaryl group $R_3$ as triazolyl, carrying the substituent $R_4$ in 4- or 5-position, and also $R_3$ as 2-thienyl carrying the substituent $R_4$ in 4- or 5-position.

An optionally substituted unsaturated alkyl group $R_3$ is 1-alkenyl carrying the further substituent $R_4$ in 1- or 2-position, preferably in 2-position, or 1-alkynyl. Substituents considered in 1-alkenyl are e.g. lower alkyl, e.g. methyl, lower alkoxy, e.g. methoxy, lower acyloxy, e.g. acetoxy, or halogenyl, e.g. chloro. In a particularly preferred embodiment of the invention $R_3$ is 1-alkynyl.

An optionally substituted unsaturated cycloalkyl group is a cycloalkenyl group with 5 to 7 carbon atoms unsaturated in 1-position, e.g. 1-cyclopentenyl or 1-cyclohexenyl, carrying the further substituent $R_4$ in any position. Substituents considered are e.g. lower alkyl, e.g. methyl, lower alkoxy, e.g. methoxy, lower acyloxy, e.g. acetoxy, or halogenyl, e.g. chloro.

An optionally substituted unsaturated heterocyclyl group has 3 to 12 atoms, 1 to 5 heteroatoms selected from nitrogen, oxygen and sulfur, and a double bond in the position connecting the heterocyclyl group to methylene $CH_2$. Substituents considered are e.g. lower alkyl, e.g. methyl, lower alkoxy, e.g. methoxy, lower acyloxy, e.g. acetoxy, or halogenyl, e.g. chloro.

In particular, an optionally substituted unsaturated heterocyclyl group is a partially saturated heteroaromatic group as defined hereinbefore for a heteroaromatic group $R_3$. An example of such a heterocyclyl group is isoxazolidinyl, especially 3-isoxazolidinyl carrying the further substituent in 5-position, or 5-isoxazolidinyl, carrying the further substituent in 3-position.

In $R_5$ with the meaning arylmethyl, aryl is preferably phenyl or naphthyl, in particular phenyl or substituted phenyl, e.g. phenyl substituted in para or meta position by lower alkyl, such as methyl or ethyl, lower alkoxy, such as methoxy, halogen, e.g. fluorine or chlorine, amino, or acylamino.

In $R_5$ with the meaning heteroarylmethyl, heteroaryl is a mono- or bicyclic heteroaryl group comprising zero, one, two, three or four ring nitrogen atoms and zero or one oxygen atom and zero or one sulfur atom, with the proviso that at least one ring carbon atom is replaced by a nitrogen, oxygen or sulfur atom, and which has 5 to 12, preferably 5 or 6 ring atoms; and which may be unsubstituted or substituted by one or more, especially one, further substituents selected from the group consisting of lower alkyl, such as methyl, lower alkoxy, such as methoxy or ethoxy, halogen, e.g. chlorine, bromine or fluorine, halogenated lower alkyl, such as trifluoromethyl, or hydroxy. Preferred as heteroaryl in heteroarylmethyl $R_5$ is heteroaryl which is described as preferred under heteroaryl $R_3$, e.g. triazolyl or 2-thienyl.

$R_5$ as optionally substituted cycloalkyl is a cycloalkyl group with 3 to 7 carbon atoms, e.g. cyclopropyl, cyclopentyl or cyclohexyl, carrying an optional substituent in any position. Substituents considered are e.g. lower alkyl, e.g. methyl, lower alkoxy, e.g. methoxy, lower acyloxy, e.g. acetoxy, or halogenyl, e.g. chloro.

$R_5$ as optionally substituted cycloalkenyl is a cycloalkenyl group with 5 to 7 carbon atoms unsaturated in any position, e.g. in 1-position, e.g. 1-cyclopentenyl or 1-cyclohexenyl, carrying an optional substituent in any position. Substituents considered are those listed under cycloalkyl $R_5$.

$R_5$ as optionally substituted heterocyclyl group is saturated or unsaturated and has 3 to 12 atoms, and 1 to 5 heteroatoms selected from nitrogen, oxygen and sulfur. Substituents considered are e.g. lower alkyl, e.g. methyl, lower alkenyl, e.g. vinyl or allyl, alkinyl, e.g. acetylenyl, aryl, e.g. phenyl, halo-lower alkyl, e.g. trifluoromethyl, hydroxyalkyl, e.g. hydroxymethyl, hydroxy, lower alkoxy, e.g. methoxy, lower acyloxy, e.g. acetoxy, carboxy, carbamoyl, lower alkoxycarbonyl, e.g. methoxycarbonyl, amino, acylamino, e.g. acetylamino, nitro, azido, cyano, lower alkyl- or amino-lower alkyl-sulfenyl, -sulfinyl or -sulfonyl, or halogenyl, e.g. chloro. Preferred heterocyclyl is e.g. tetrahydrofuranyl, e.g. 2-tetrahydrofuranyl.

$R_5$ as defined hereinbefore might have one or more chiral centres, e.g. as in 2-tetrahydrofuranyl, leading to a selective recognition of only one enantiomer (or diastereomer) by wild type hAGT.

Preferred $R_5$ is cyclopentyl, cyclohexyl, benzyl, hydroxy-substituted cyclopentyl, cyclohexyl or benzyl, and hydroxy- or hydroxy-lower alkyl substituted tetrahydrofuranyl.

The labels $L_1$ and $L_2$ of the substrate can be chosen by those skilled in the art dependent on the application for which the fusion protein is intended. Labels may be e.g. such that the labelled fusion protein carrying label $L_1$ is easily detected or separated from its environment. Other labels considered are those which are capable of sensing and inducing changes in the environment of the labelled fusion protein and/or the substrate, or labels which aid in manipulating the fusion protein by the physical and/or chemical properties of the substrate and specifically introduced into the fusion protein.

Examples of labels $L_1$ and $L_2$ include a spectroscopic probe such as a fluorophore or a chromophore, a magnetic probe or a contrast reagent; a radioactively labelled molecule; a molecule which is one part of a specific binding pair which is capable of specifically binding to a partner; a molecule that is suspected to interact with other biomolecules; a library of molecules that are suspected to interact with other biomolecules; a molecule which is capable of crosslinking to other molecules; a molecule which is capable of generating hydroxyl radicals upon exposure to $H_2O_2$ and ascorbate, such as a tethered metal-chelate; a molecule which is capable of generating reactive radicals upon irradiation with light, such as malachite green; a molecule covalently attached to a solid support, where the support may be a glass slide, a microtiter plate or any polymer known to those proficient in the art; a nucleic acid or a derivative thereof capable of undergoing base-pairing with its complementary strand; a lipid or other hydrophobic molecule with membrane-inserting properties; a biomolecule with desirable enzymatic, chemical or physical properties; or a molecule possessing a combination of any of the properties listed above.

Further labels $L_1$ and $L_2$ are positively charged linear or branched polymers which are known to facilitate the transfer of attached molecules over the plasma membrane of living cells. This is of particular importance for substances which otherwise have a low cell membrane permeability or are in effect impermeable for the cell membrane of living cells. A non cell permeable AGT substrate will become cell membrane permeable upon conjugation to such a group $L_1$ or $L_2$. Such cell membrane transport enhancer groups $L_1$ and $L_2$ comprise, for example, a linear poly(arginine) of D- and/or L-arginine with 6-15 arginine residues, linear polymers of 6-15 subunits which each carry a guanidinium group, oligomers or short-length polymers of from 6 up to 50 subunits, a portion of which have attached guanidinium groups, and/or parts of the sequence of the HIV-tat protein, in particular the subunit Tat49-Tat57 (RKKRRQRRR in the one letter amino acid code). The AGT substrate is covalently linked to this group $L_1$ or $L_2$ through a linker $R_2$ or $R_4$ as defined hereinbefore, which is preferably labile inside a living cell and may be degraded, e.g. by cleavage of an ester group $R_2$ or $R_4$ by intracellular esterases, leading directly or in a further reaction provoked by the cleavage of the ester function to a separation of the AGT substrate and the unit $L_1$ and $L_2$ enhancing cell membrane permeability.

Preferred are labels $L_1$ and $L_2$ as mentioned hereinbefore with the exception of a radioactively labelled molecule. Excluded from the scope are labels $L_2$ with the meaning of a nucleic acid. Most preferred as labels $L_1$ are spectroscopic probes, and molecules which are one part of a specific binding pair which is capable of specifically binding to a partner, so-called affinity labels. Most preferred as labels $L_2$ are molecules representing one part of a specific binding pair which is capable of specifically binding to a partner, and molecules covalently attached to a solid support.

When the label $L_1$ or $L_2$ is a fluorophore, a chromophore, a magnetic label, a radioactive label or the like, detection is by standard means adapted to the label and whether the method is used in vitro or in vivo. If $L_1$ is a fluorophore the method can be compared to the applications of the green fluorescent protein (GFP) which is genetically fused to a protein of interest and allows protein investigation in the living cell. Particular examples of labels $L_1$ and $L_2$ are also boron compounds displaying non-linear optical properties. Particularly preferred are labels such that $L_1$ is one member and $L_2$ is the other member of two interacting spectroscopic probes $L_1/L_2$, wherein energy can be transferred nonradiatively between the donor and acceptor (quencher) when they are in close proximity (less than 10 nanometer distance) through either dynamic or static quenching. Such a pair of labels $L_1/L_2$ changes its spectroscopic properties on reaction of the labelled substrate with the AGT fusion protein. An example of such a pair of labels $L_1/L_2$ is a FRET pair explained below in more detail.

Depending on the properties of the label $L_1$, the fusion protein comprising protein of interest and AGT may be bound to a solid support on reaction with the substrate. The label $L_1$ of the substrate reacting with the fusion protein comprising AGT may already be attached to a solid support when entering into reaction with AGT, or may subsequently, i.e. after transfer to AGT, be used to attach the labelled AGT fusion protein to a solid support. Alternatively, the label $L_2$ of the substrate may be a solid support or attached or attachable to a solid support, which allows separating the labelled fusion protein carrying label $L_1$ from the remaining part of the substrate after reaction and containing $L_2$. The label may be one member of a specific binding pair, the other member of which is attached or attachable to the solid support, either covalently or by any other means. A specific binding pair considered is e.g. biotin and avidin or streptavidin. Either member of the binding pair may be the label $L_1$ and/or $L_2$ of the substrate, the other being attached to the solid support. Further examples of labels allowing convenient binding to a solid support are e.g. maltose binding protein, glycoproteins, FLAG tags, or reactive substituents allowing chemoselective reaction between such substituent with a complementary functional group on the surface of the solid support. Examples of such pairs of reactive substituents and complementary functional group are e.g. amine and activated carboxy group forming an amide, azide and a propiolic acid derivative undergoing a 1,3-dipolar cycloaddition reaction, amine and another amine functional group reacting with an added bifunctional linker reagent of the type of activated bis-dicarboxylic acid derivative giving rise to two amide bonds, or other combinations known in the art.

Examples of a convenient solid support are e.g. glass surfaces such as glass slides, microtiter plates, and suitable sensor elements, in particular functionalized polymers (e.g. in the form of beads), chemically modified oxidic surfaces, e.g. silicon dioxide, tantalum pentoxide or titanium dioxide, or also chemically modified metal surfaces, e.g. noble metal surfaces such as gold or silver surfaces. Irreversibly attaching and/or spotting AGT substrates may then be used to attach AGT fusion proteins in a spatially resolved manner, particularly through spotting, on the solid support representing protein microarrays, DNA microarrays or arrays of small molecules.

When the label $L_1$ or $L_2$ is capable of generating reactive radicals, such as hydroxyl radicals, upon exposure to an external stimulus, the generated radicals can then inactivate the AGT fusion proteins as well as those proteins that are in close proximity of the AGT fusion protein, allowing to study the role of these proteins. Examples of such labels are tethered metal-chelate complexes that produce hydroxyl radicals upon exposure to $H_2O_2$ and ascorbate, and chromophores such as malachite green that produce hydroxyl radicals upon laser irradiation. The use of chromophores and lasers to generate hydroxyl radicals is also known in the art as chromophore assisted laser induced inactivation (CALI). In the present invention, labeling AGT fusion proteins with substrates carrying chromophores as label $L_1$, such as malachite green, and subsequent laser irradiation inactivates the labelled AGT fusion protein as well as those proteins that interact with the AGT fusion protein in a time-controlled and spatially-resolved manner. This method can be applied both in vivo or in vitro. Furthermore, proteins which are in close proximity of the AGT fusion protein can be identified as such by either detecting fragments of that protein by a specific antibody, by the disappearance of those proteins on a high-resolution 2D-electrophoresis gels or by identification of the cleaved protein fragments via separation and sequencing techniques such as mass spectrometry or protein sequencing by N-terminal degradation.

When the label $L_1$ is a molecule that can cross-link to other proteins, e.g. a molecule containing functional groups such as maleimides, active esters or azides and others known to those proficient in the art, contacting such labelled AGT substrates with AGT fusion proteins that interact with other proteins (in vivo or in vitro) leads to the covalent cross-linking of the AGT fusion protein with its interacting protein via the label. This allows the identification of the protein interacting with the AGT fusion protein. Labels $L_1$ (and $L_2$) for photo cross-linking are e.g. benzophenones. In a special aspect of cross-linking the label $L_1$ is a molecule which is itself an AGT substrate leading to dimerization of the AGT fusion protein. The chemical structure of such dimers may be either symmetrical (homodimers) or unsymmetrical (heterodimers).

Other labels $L_1$ considered are for example fullerenes, boranes for neutron capture treatment, nucleotides or oligonucleotides, e.g. for self-addressing chips, peptide nucleic acids, and metal chelates, e.g. platinum chelates that bind specifically to DNA.

A particular biomolecule with desirable enzymatic, chemical or physical properties is methotrexate. Methotrexate is a tight-binding inhibitor of the enzyme dihydrofolate reductase (DHFR). Compounds of formula (1) wherein $L_1$ is methotrexate belong to the well known class of so-called "chemical inducers of dimerization" (CIDs). Using fusion proteins of hAGT with the DNA-binding domain LexA, and adding DHFR with the transcriptional activation domain B42 to the in vivo labeling of the hAGT fusion protein with a compound of formula (1) wherein $L_1$ is methotrexate induces the coupling ("dimerization") of the hAGT-LexA fusion protein and DHFR-B42 fusion protein, leading to spatial proximity of LexA and B42 and subsequent stimulation of transcription.

If the substrate carries two or more labels, these labels may be identical or different. Particular preferred combinations are two different affinity labels, or one affinity label and one chromophore label, in particular one affinity label and one fluorophore label, or a pair of spectroscopic interacting labels $L_1/L_2$, e.g. a FRET pair.

Preferred are compounds of formula (1) wherein X is oxygen. Further preferred are compounds wherein X is oxygen and $R_3$ is phenyl, in particular para-substituted phenyl, or thienyl, in particular 2,4-disubstituted thienyl.

Likewise preferred are compounds of formula (1) wherein the group $R_1$-A is a purine radical of formula (2), wherein $R_6$ is hydrogen, hydroxy or unsubstituted or substituted amino, preferably unsubstituted amino; and one of $R_7$ and $R_8$ is $R_1$ and the other one is hydrogen. If $R_7$ is $R_1$, $R_1$ may be a group —$R_2$-$L_2$ or a residue $R_5$. Particularly preferred are corresponding compounds wherein $R_8$ is $R_1$ and $R_1$ is a group —$R_2$-$L_2$. If $R_1$ is a residue $R_5$, the preferred meaning of $R_5$ is cyclopentyl.

Other preferred compounds are those of formula (1) wherein the group $R_1$-A is an 8-azapurine radical of formula (3), wherein the substituent $R_6$ is hydrogen, hydroxy or unsubstituted or substituted amino, preferably unsubstituted amino;

a pyrimidine radical of formula (4a) or (4b), wherein $R_9$ is hydrogen, halogen, lower alkyl with 1 to 4 carbon atom or amino, and $R_{10}$ is hydrogen, halogen, lower alkyl with 1 to 4 carbon atoms, amino, nitro or nitroso; and a pteridine radical of formula (4c), wherein $R_6$ is unsubstituted or substituted amino, preferably unsubstituted amino; and one of $R_7$ and $R_8$ is $R_1$ and the other one is hydrogen. Preferably, $R_7$ is hydrogen and $R_8$ is a group —$R_2$-$L_2$.

Preferred are compounds wherein $L_2$ is a spectroscopic probe, in particular wherein both $L_1$ and $L_2$ are spectroscopic probes, for example representing a FRET pair. Likewise preferred are compounds wherein $L_2$ is a molecule representing one part of a specific binding pair, compounds wherein $L_2$ is a molecule covalently attached to a solid support, and compounds wherein $L_2$ is a cell membrane transport enhancer group.

Most preferred are the compounds of the Examples.

The invention further relates to a method for detecting and/or manipulating a protein of interest, wherein the protein of interest is incorporated into an AGT fusion protein, the AGT fusion protein is contacted with particular AGT substrates carrying a label described hereinbefore, and the AGT fusion protein is detected and optionally further manipulated using the label in a system designed for recognising and/or handling the label.

In the method of the present invention a protein or peptide of interest is fused to an $O^6$-alkylguanine-DNA alkyltransferase (AGT). The protein or peptide of interest may be of any length and both with and without secondary, tertiary or quaternary structure, and preferably consists of at least twelve amino acids and up to 2000 amino acids. Examples of such protein or peptide of interest are e.g. enzymes, DNA-binding proteins, transcription regulating proteins, membrane proteins, nuclear receptor proteins, nuclear localization signal proteins, protein cofactors, small monomeric GTPases, ATP-binding cassette proteins, intracellular structural proteins, proteins with sequences responsible for targeting proteins to particular cellular compartments, proteins generally used as labels or affinity tags, and domains or subdomains of the aforementioned proteins. The protein or peptide of interest is preferably fused to AGT by way of a linker which may be cleaved by an enzyme, e.g. at the DNA stage by suitable restriction enzymes and/or linkers cleavable by suitable enzymes at the protein stage.

The $O^6$-alkylguanine-DNA alkyltransferase (AGT) has the property of transferring a label present on a substrate to one of the cysteine residues of the AGT forming part of a fusion protein. In preferred embodiments, the AGT is wild type human $O^6$-alkylguanine-DNA alkyltransferase, hAGT, or a mutant thereof, e.g. a mutant as described in Juillerat et al., Chem Biol 10:313-317, 2003, or in the Examples hereinafter. A mutant AGT to be used in the invention may differ from wild type hAGT by virtue of one or more amino acid substitutions, deletions or additions, but still retains the property of transferring a label present on a substrate to the AGT part of the fusion protein. A mutant AGT may preferably be produced using protein engineering techniques known to the skilled person in the art, e.g. saturation mutagenesis, error prone PCR to introduce variations anywhere in the sequence, or DNA shuffling used after saturation mutagenesis and/or error prone PCR.

The fusion protein comprising protein of interest and an $O^6$-alkylguanine-DNA alkyl-transferase (AGT) is contacted with a particular substrate having a label. Conditions of reaction are selected such that the AGT reacts with the substrate and transfers the label of the substrate. Usual conditions are a buffer solution at around pH 7 at room temperature, e.g. around 25° C. However, it is understood that AGT reacts also under a variety of other conditions, and those conditions mentioned here are not limiting the scope of the invention.

The reaction rate is very much dependent on the structure of the substrate. The compounds described in this invention show differences in reactivity, and these differences may be used to selectively react compounds of the invention with different $O^6$-alkylguanine-DNA alkyltransferases (AGTs), e.g. wild type AGTs from different species, or, in particular, AGT mutants wherein some of the amino acids of the wild type AGT are replaced by different amino acids, as demonstrated in the Examples.

Reactivity differences are, for example, found in compounds of formula (1) wherein X is oxygen, $R_3$ is para-substituted phenyl, the group $R_1$-A is a purine radical of formula (2), wherein $R_6$ is unsubstituted amino; and one of $R_7$ and $R_8$ is a group —$R_2$-$L_2$ and the other one is hydrogen. Such compounds wherein $R_7$ is hydrogen and $R_8$ is a group —$R_2$-$L_2$ react at least a factor of three more rapid than corresponding compounds wherein $R_7$ is a group —$R_2$-$L_2$ (e.g. the same group —$R_2$-$L_2$) and $R_8$ is hydrogen, and also more rapidly than compounds wherein both $R_7$ and $R_8$ are hydrogen.

AGT irreversibly transfers the alkyl group from its natural substrate, $O^6$-alkylguanine-DNA, to one of its cysteine residues. Likewise, AGT transfers the guanine type $O^6$ substituent or the corresponding substituent in a related position of the substrates of the invention to one of its cysteine residues. This property of AGT is used in the method of the invention to transfer the label $L_1$ attached to the residue $CH_2$—$R_3$—$R_4$— of a compound of formula (1) to AGT.

This label $L_1$ of the substrate can be chosen by those skilled in the art dependent on the application for which the fusion protein is intended. After contacting the fusion protein comprising AGT with the substrate, the label $L_1$ is covalently bonded to the fusion protein. The labelled AGT fusion protein is then further manipulated and/or detected by virtue of the transferred label. The label $L_1$ may consist of a plurality of same or different labels. If the substrate contains more than one label $L_1$, the corresponding labelled AGT fusion protein will also comprise more than one label which gives more options for further manipulating and/or detecting the labelled fusion protein.

In a particular aspect, the present invention provides a particularly convenient method to transfer a label $L_1$ to the AGT fusion protein and to remove all unreacted AGT substrate. This is simply done in the case when label $L_2$ connected through $R_2$ to the heterocyclic group A recognized by AGT as a substrate is a label $L_2$ with the meaning of a solid support or the meaning of a reactive group attachable to a solid support, e.g. one part of a specific binding pair which is capable of specifically binding to a partner attached to a solid support. The solid support and the protein solution containing the AGT fusion protein labelled with $L_1$ are then easily separated, e.g. by filtration, without further manipulation. More specifically, a molecular excess of substrate of the formula (1) wherein $R_1$ is $R_2$-$L_2$ and $L_2$ is a solid support or a group attached to a solid support is reacted with an AGT fusion protein, and the obtained labelled AGT fusion protein carrying a label $L_1$ is separated from the solid support to which the remaining part of the reacted substrate, i.e. the residue $R_2$-A, is bound, and also to which the excess unreacted substrate of formula (1) remains bound. In other terms the AGT fusion protein, on reacting with the substrate, removes and takes over the label $L_1$ from a solid support, leaving all unreacted label $L_1$ bound to the solid support.

In this particular aspect the label $L_1$ may be any label as described hereinbefore, for example a spectroscopic probe or a fluorophore. The solid support, i.e. $L_2$ or the support to which $L_2$ is attached, may be any solid support, for example a bead (e.g. a magnetic bead), a polymer support or a metal surface. Separation of the labelled AGT fusion protein from unreacted substrate may be by filtration, centrifugation or other suitable methods depending on the properties of the solid support, e.g. applying a magnetic field if the solid support is a magnetic bead.

In another particular aspect of the invention a method is provided which makes use of a spatial separation of labels $L_1$ and $L_2$ on reaction with an AGT fusion protein. Particular substrates of the present invention are designed as interacting spectroscopic labels, e.g. pro-fluorescent probes covalently labeled at one end (e.g. $L_1$) with a donor (reporter) and at the other end ($L_2$) with an acceptor (quencher), and vice versa. It is generally known that quenching in such probes may occur through Förster resonance energy transfer (FRET) or through static quenching by close proximity of the donor acceptor pair. The donor and acceptor should be chosen such as to maximize their spectral overlap. Förster energy transfer typically occurs over distances of up to 20-100 Å.

In the particular method of the invention, wherein $L_1$ is a donor (reporter) and $L_2$ is an acceptor (quencher), or wherein $L_1$ is a quencher and $L_2$ is a reporter the reaction of the AGT fusion protein with the substrate leads to a change in fluorescence. The reporter-quencher distance within the doubly labeled substrate is changed upon reaction with the AGT fusion protein leading to a spatial separation of reporter and quencher witch causes the appearance of fluorescence. A broad selection of reporter groups may be used as the label $L_1$ or $L_2$, respectively, including e.g. infra-red emitting fluorophores, and the sensitivity and specificity of the method is substantially improved compared to substrates carrying only one fluorophore label $L_1$. The substrate containing reporter and quencher remains dark until it reacts with the AGT fusion protein, whereupon the reaction mixture is "lit up" switching on the fluorophore emission, since the reporter label and the quencher label are now spatially separated. Fluorescence quenching and energy transfer can be measured by the emission of only one of the two labels, the quenched or energy donor label. When energy transfer occurs and the energy accepting label is also fluorescent, the acceptor label fluorescence can also be measured. A donor label of these two interacting labels can be chosen from chemiluminescent donor probes which eliminates the need of an excitation lamp and reduces acceptor background fluorescence. The mentioned particular method using such double-labelled substrates is useful to determine reaction kinetics based on fluorescence time measurements, and may be applied in vivo as well as in vitro.

In vitro, the reaction of the AGT fusion protein with the substrate of the invention can generally be either performed in cell extracts or with purified or enriched forms of the AGT fusion protein.

If experiments with the substrates of the present invention are done in vivo or in cell extracts, the reaction of the endogenous AGT of the host is advantageously taken into account. If the endogenous AGT of the host does not accept $O^6$-alkylguanine derivatives or related compounds as a substrate, the reaction of the (exogenous) AGT fusion protein is specific. In mammalian cells, e.g. in human, murine, or rat cells, unspecific reaction with endogenous AGT is possible. In those experiments where the simultaneous reaction of the endogenous AGT as well as of the (exogenous) AGT fusion protein poses a problem, known AGT-deficient cell lines can be used.

In the described particular embodiment of the invention, the doubly labelled substrates carrying reporter and quencher allow to determine the concentration of AGT fusion proteins either in vitro or in vivo. For in vivo application, the reporters are preferably emitters in the near infra red (NIR) region because that region is absent of interfering bio fluorescence. Known cyanine NIR dyes matching these requirements are preferably incorporated in the substrates of the present invention.

Appropriate pairs of reporters and quenchers can bee chosen by those skilled in the art. Typically reporter and quencher are fluorescent dyes with large spectral overlap as, for example, fluorescein as a reporter and rhodamine as a quencher. Other quenchers are gold clusters, and metal cryptates.

A second class of quenchers used in this invention are "dark quenchers" (Johnasson, M. K. et al., Chem. Eur. J. 9:3466-3471, 2003), i.e. dyes without native fluorescence having absorption spectra that overlap with the emission spectra of common reporter dyes leading to maximal FRET quenching. Furthermore pairs of dyes can be chosen such that their absorption bands overlap in order to promote a resonance dipole-dipole interaction mechanism within a ground state complex (static quenching).

Particular fluorophores and quenchers considered are: Alexa dyes, including Alexa 350, Alexa 488, Alexa 532, Alexa 546, Alexa 555, Alexa 635 and Alexa 647 (Panchuk-Voloshina, N. et al., J. Histochem. & Cytochem. 47:1179-1188, 1999); dimethylamino-coumarin (7-dimethylaminocoumarin-4-acetic acid succinimidyl ester supplied as product D374 by Moelcular Probes); quenchers QSY 35, QSY 9 and QSY 21 (Molecular Probes, Inc., Eugene, Oreg. 97402, USA); Cyanine-3 (Cy 3), Cyanine 5 (Cy 5) and Cyanine 5.5 (Cy 5.5) (Amersham-GE Healthcare, Solingen, Germany); BHQ-1, BHQ-2 and BHQ-3 (Black Hole Quencher™ of Biosearch Technologies, Inc., Novato, Calif. 94949, USA); fluorophores ATTO 488, ATTO 532, ATTO 600 and ATTO 655 and quenchers ATTO 540Q and ATTO 612Q (Atto-Tec, D57076 Siegen, Germany); fluorophores DY-505, DY-547, DY-632 and DY-647 (Dyomics, Jena, Germany); 5/6-carboxy-fluorescein, tetramethylrhodamine, 4-dimethylaminoazobenzene-4'-sulfonyl derivatives (Dabsyl) and 4-dimethylaminoazobenzene-4'-carbonyl derivatives (Dabcyl). These will be advantageously combined in the following combinations:

| Fluorophore | Quencher |
|---|---|
| Alexa 350, dimethylaminocoumarin, 5/6-carboxy-fluorescein, Alexa 488, ATTO 488, DY-505 | Dabsyl, Dabcyl, BHQ 1, QSY 35 |
| 5/6-carboxyfluorescein, Alexa 488, Alexa 532, Alexa 546, Alexa 555, ATTO 488, ATTO 532, tetramethylrhodamine, Cy 3, DY-505, DY-547, | BHQ 2, QSY 9, ATTO 540Q |
| Alexa 635, Alexa 647, ATTO 600, ATTO 655, DY-632, Cy 5, DY-647 Cy 5.5 | BHQ 3, ATTO 612Q, QSY 21 |

In a particular embodiment, the method involves a substrate wherein $L_2$ is a solid support or attached to a solid support further carrying one member of the reporter/quencher pair, or wherein $L_2$ is a combination of a solid support and one member of the reporter/quencher pair, and $L_1$ is the other member of this pair. In this way, the dark solid support being an AGT substrate becomes fluorescent upon reaction with the AGT fusion protein.

The mentioned particular method involving fluorescence determination based on a reporter/quencher pair, e.g. a FRET pair, is much more convenient than other methods for measuring the concentration or the kinetics of reactivity based on SDS/PAGE, Western blotting or the like, which require considerable protein preparation and manipulation of conditions to remove non-specific signals. The energy transfer method does not require separation of reacted and unreacted AGT substrate. Therefore this method is particularly convenient for high-throughput screening of compound libraries, identification of active AGT mutants or identification of AGT inhibitors.

In a further particular method of the invention, a substrate is used wherein $R_1$ is a group $R_5$, in particular a cycloalkyl, cycloalkenyl, cycloalkylmethyl, arylmethyl or heteroarylmethyl group. Examples of preferred groups $R_5$ are cyclopentyl and benzyl. In the AGT fusion protein, a mutant AGT is chosen as fusion partner which has a low reactivity towards substrates wherein $R_5$ is one of the mentioned particular or preferred substituents. In such a particular method for detecting and/or manipulating a protein of interest, the protein of interest is fused with the mutant AGT, the mutant AGT fusion protein is contacted with a mixture of (a) a substrate wherein $R_1$ is a group $R_5$ and which is not recognized by the mutant AGT, and (b) another AGT substrate recognized by the mutant AGT fusion protein, and carrying a label described hereinbefore, and the mutant AGT fusion protein is detected and optionally further manipulated using the label in a system designed for recognizing and/or handling the label. Such a method is the method of choice if the reaction is carried out in vivo in a system comprising endogenous AGT, or carried out in cell extracts comprising endogenous AGT. The endogenous AGT is saturated, and if required, separated using the label $L_1$ of the substrate of the invention wherein $R_1$ is a group $R_5$. In a parallel reaction the mutant AGT fusion protein reacts with another AGT substrate carrying a label or a plurality of labels as described hereinbefore, and detected and/or manipulated as required.

Method of Manufacture

Substrates of the invention are generally prepared by standard methods known in the art. Particular methods are explained e.g. in patent application PCT/EP03/10889. For the synthesis of a substrate of formula (2), i.e. compounds wherein A is a purine entity, known methods can be used to modify the $O^6$, $C^8$ and $N^9$ position. The present invention also relates to new methods as described hereinafter, and to novel intermediates used and obtained.

In particular, the preferred synthesis of a AGT substrate carrying a plurality of labels (e.g. $L_1$ and $L_2$) makes use of orthogonally protected functional groups. Such a choice of protective groups allows for a separate deprotection so that each released functionality in turn can be further chemically manipulated either to attach a label to it or for the introduction of further extension of the linker $R_2$ and/or $R_4$. Appropriate protecting groups for the envisioned functionalities can be chosen by those skilled in the art, and are e.g. summarized in T. W. Greene and P. G. M. Wuts in "Protective Groups in Organic Synthesis", John Wiley & Sons, New York 1991.

For the preparation of guanine derivatives, the group —$CH_2$—$R_3$—$R_4$-$L_1$ or a precursor thereof is introduced on reaction of a corresponding 6-chloroguanine derivative via the intermediacy of an ammonium salt with a tertiary amine, e.g. methylpyrrolidine. Displacement of the ammonium group by an alcoholate $^-O$—$CH_2$—$R_3$—$R_4$-$L_1$ or a precursor thereof gives higher overall yields compared to the direct displacement of chlorine, and the reaction with ammonium salts can be performed at room temperature.

Introduction of a group $R_1$ at position $N^9$ of a guanine of formula (2) may be performed by direct alkylation via $SN_2$ reaction using halogen derivatives $R_1$-Hal. However, regioselectivity is generally poor, and a product mixture of $N^7$ and $N^9$ alkylated guanines is obtained. A higher $N^9/N^7$ ratio in the alkylated product is obtained on activating the imidazole ring by pre-treatment with LiH, or by equilibrating the obtained product at higher temperatures which favors the $N^9$ substitution. The preparation of a convenient intermediate of formula (5) is shown in Scheme 1:

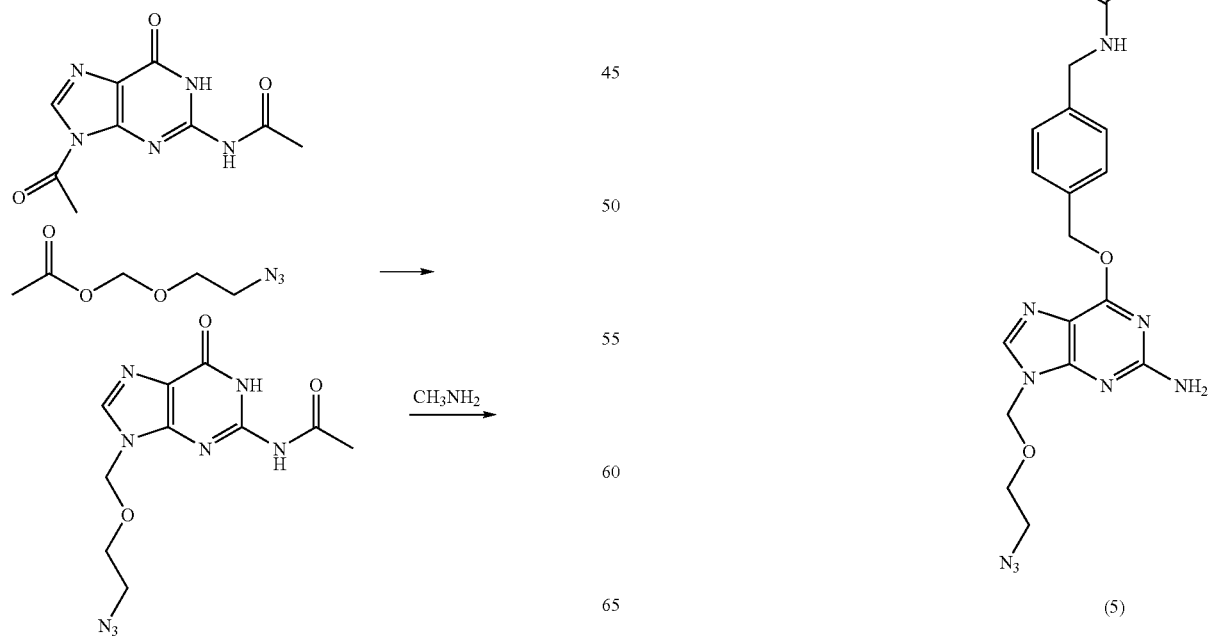

Scheme 1

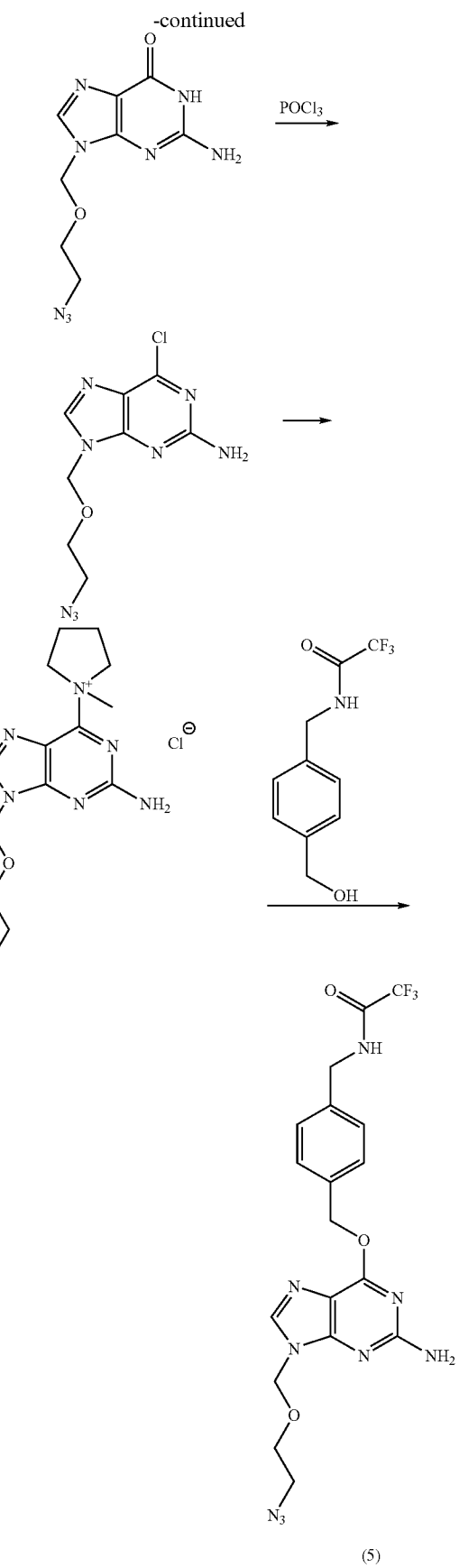

(5)

The intermediate of formula (5) is orthogonally protected at the linker in $N^9$ and at the benzyl function in position $O^6$. This intermediate may then be further manipulated to complete the residue —$R_4$-$L_1$ at the benzyl function in $O^6$ and the residue —$R_2$-$L_2$ at the position $N^9$. Alternatively Mitsunobu conditions (alcohol derivative $R_1$—OH, triphenylphosphine, diethyl azodicarboxylate) may be used to introduce a substituent $R_1$ (i.e. $R_5$ or —$R_2$-$L_2$) in position $N^9$.

The synthesis of a compound closely related to intermediate (5) but carrying an azidopropyl group in position $N^9$ is illustrated in the experimental part, Examples 8 to 10.

Scheme 2

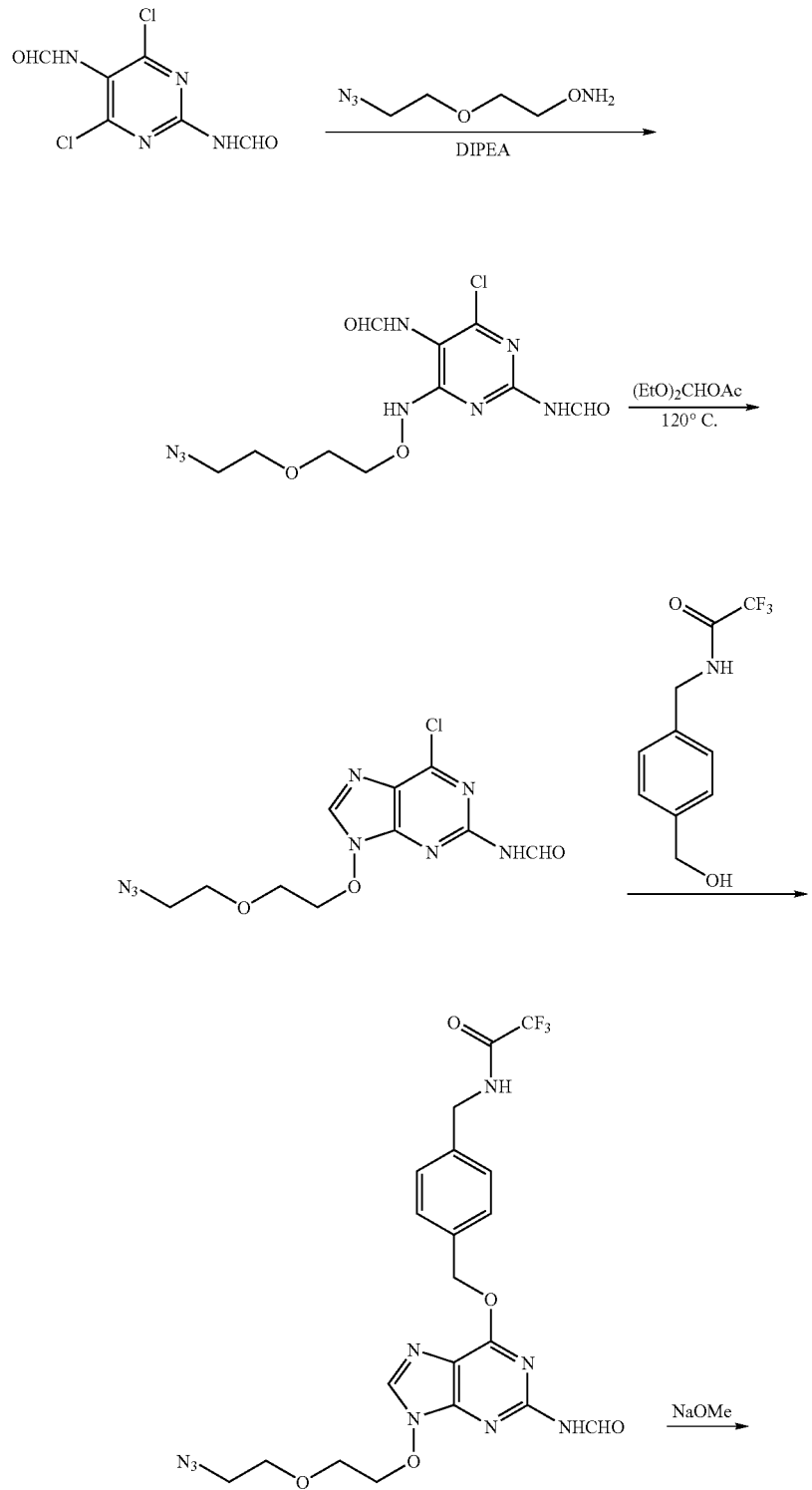

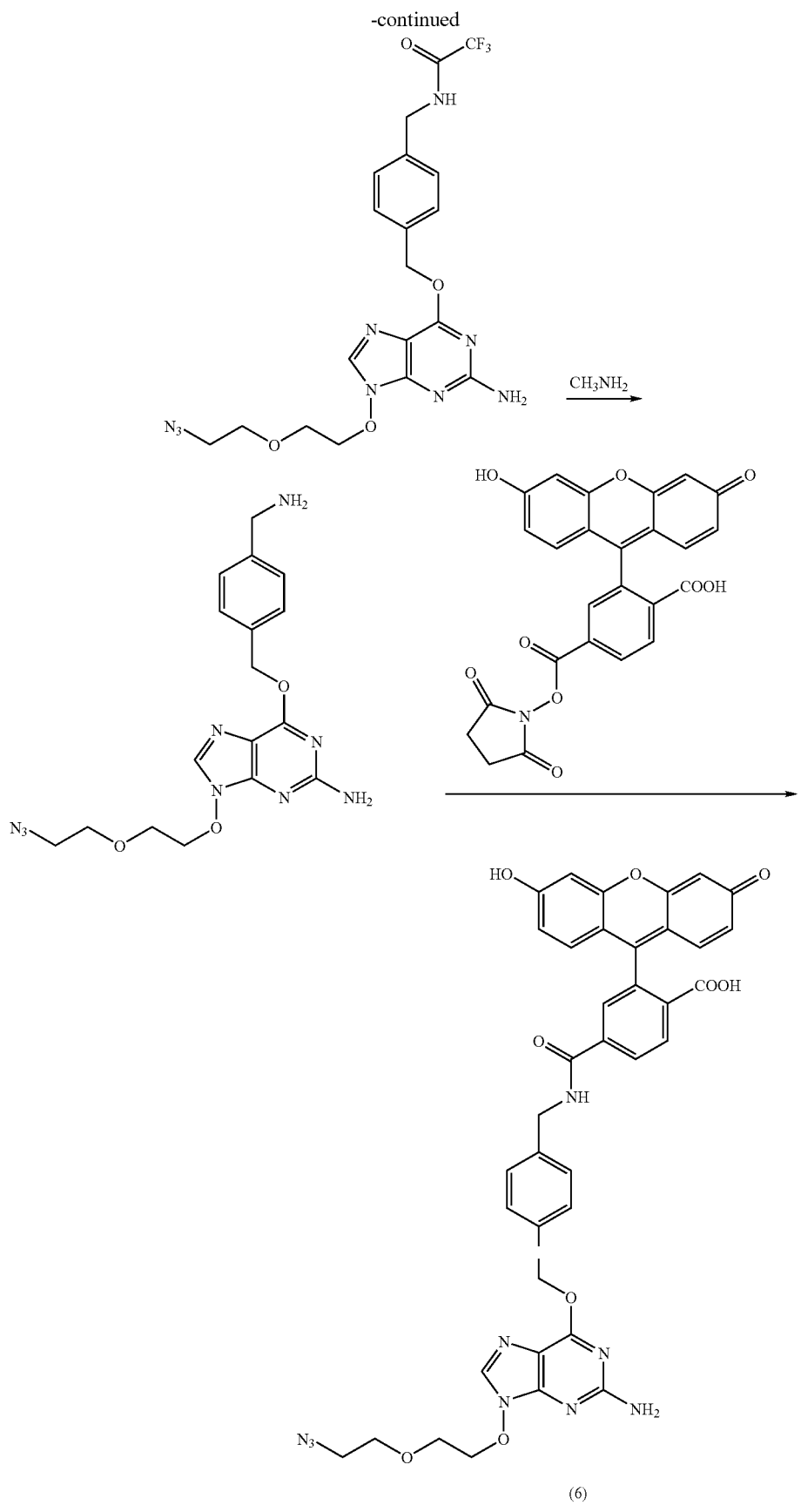

Scheme 2 demonstrates a ring closure reaction leading to regioselective introduction of a substituent in position $N^9$. Intermediate of formula (6) already contains a label $L_1$ and allows the introduction of a suitable label $L_2$ by modification of the azido function.

Reduction of the azido function in the compound of formula (6) with triphenylphosphine and acylation with QSY-9-NHS (Molecular Probes) gives the pro-fluorescent AGT substrate of formula (7), wherein $L_1$ (carboxy-fluorescein) and $L_2$ (QSY-9) represent a FRET pair (Scheme 3).

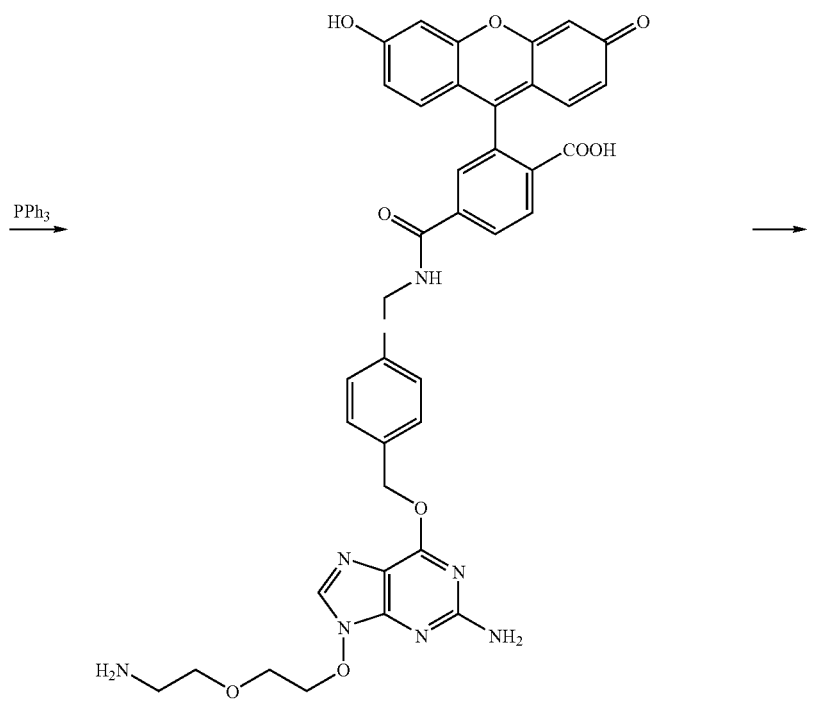

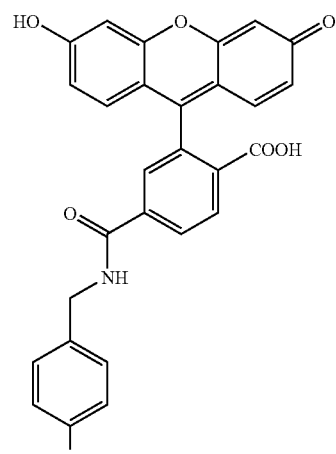

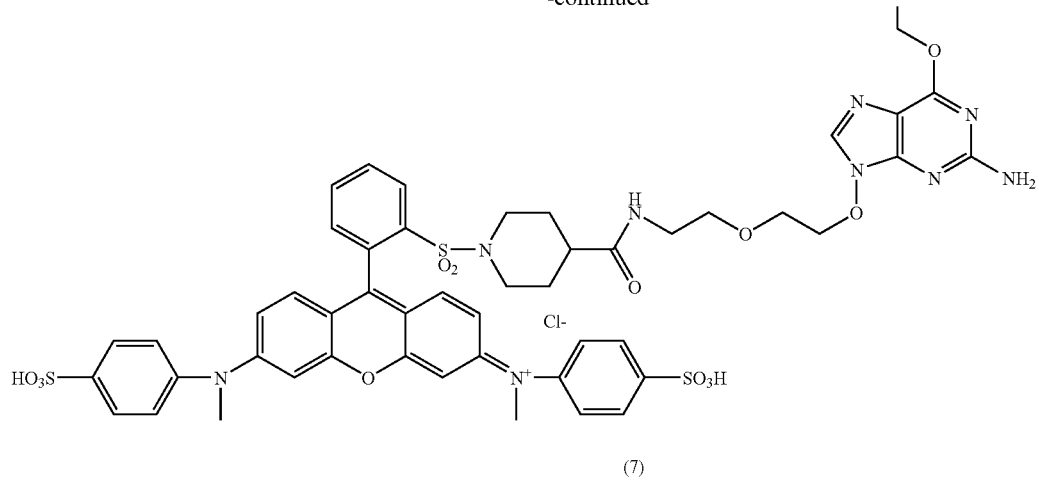

(7)

Further compounds of the type (7) carrying labels $L_1$ and $L_2$ in position $O^6$ and $N^9$, respectively, and representing a FRET pair are described in Examples 14, 15 and 19 hereinbelow.

A further method for regioselective alkylation in $N^9$ is palladium catalyzed allylic alkylation as shown in Scheme 4.

For structural modifications at the level of the linker moiety $R_2$, the synthesis of appropriate functionalized homo-N,O-nucleosides, wherein the sugar moiety of guanosine is replaced by an isoxazolidine ring, is likewise shown in Scheme 4 (TBDPS=tert-butyl-diphenyl-silyl). Such modifications introduce an increased resistance to hydrolytic or enzymatic cleavage compared to the relatively reactive aminal linkage of common nucleosides and more conformational flexibility. The reaction sequence is versatile, allowing for the attachment of different appropriate functionalized nitrones to allyl double bond.

Alternatively, the allyl group at $N^9$ may be transformed into a primary hydroxy function with the boron hydride reagent 9-borabicyclo[3.3.1]nonane (9-BBN), and then further manipulated to give appropriate groups $R_5$ or —$R_2$-$L_2$.

Scheme 4

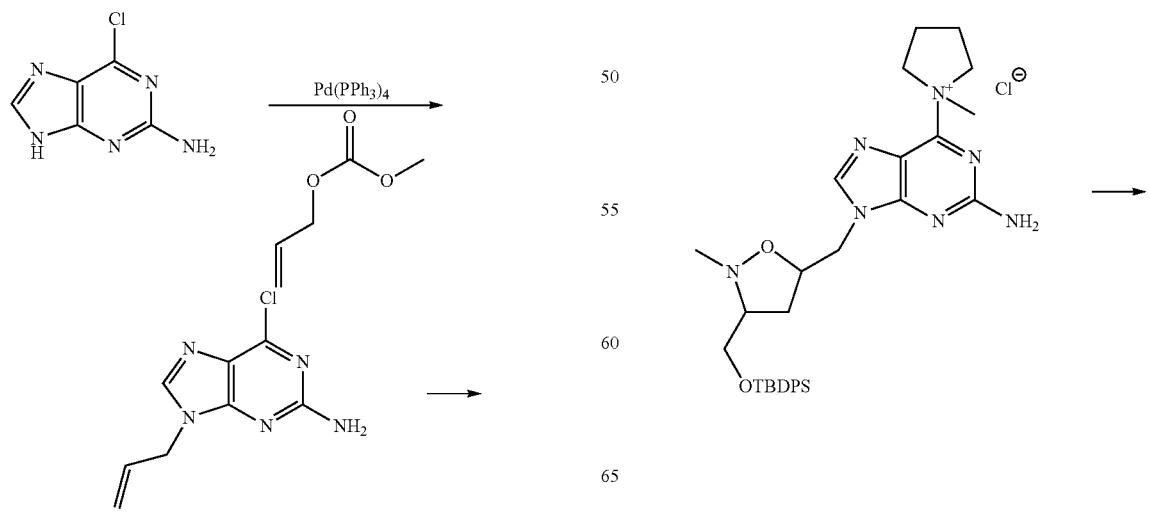

-continued

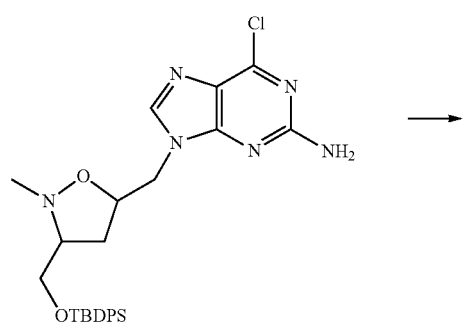

-continued
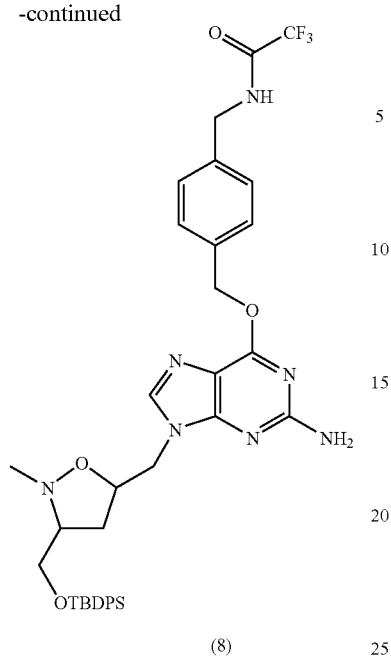
(8)
Scheme 5
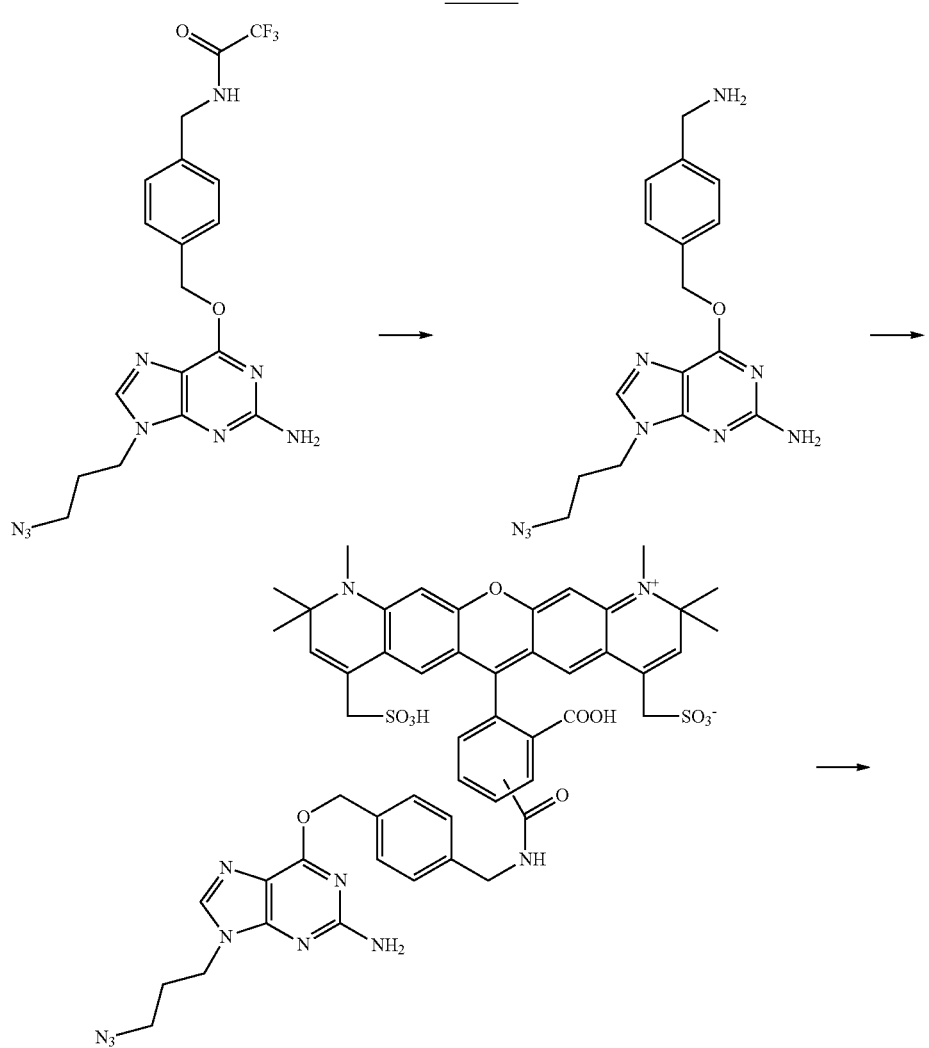

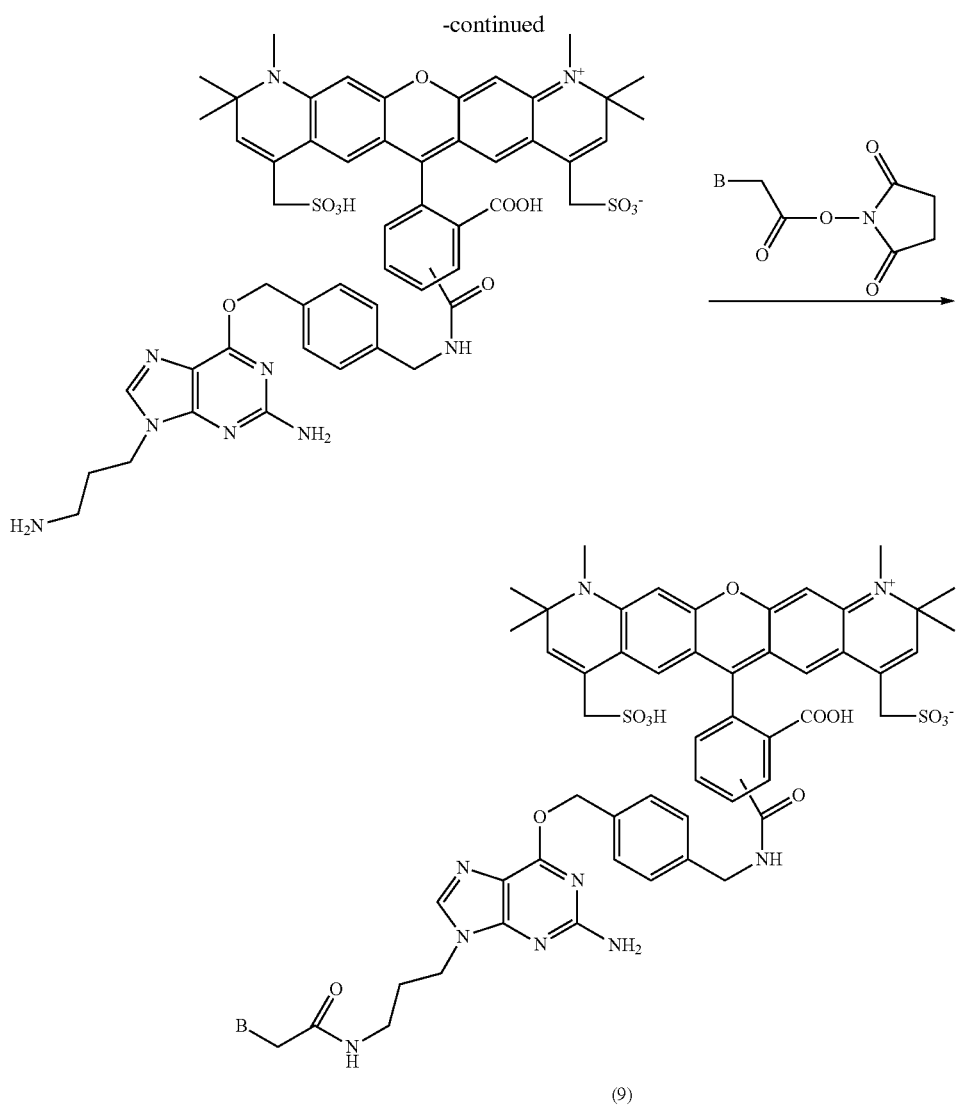

The synthesis of a substrate of the invention of formula (9) wherein $L_1$ is a fluorophore (Alexa 594, Molecular Probes) and $L_2$ is a solid support (e.g. a bead B, or a biotin residue B attachable to a bead carrying avidin or streptavidin) is summarized in Scheme 5.

The synthesis of intermediates useful in the synthesis of a compound of formula (1) wherein two different labels are attached in $O^6$ and $C^8$ position of the purine base is summarized in Schemes 6 and 7. Scheme 6

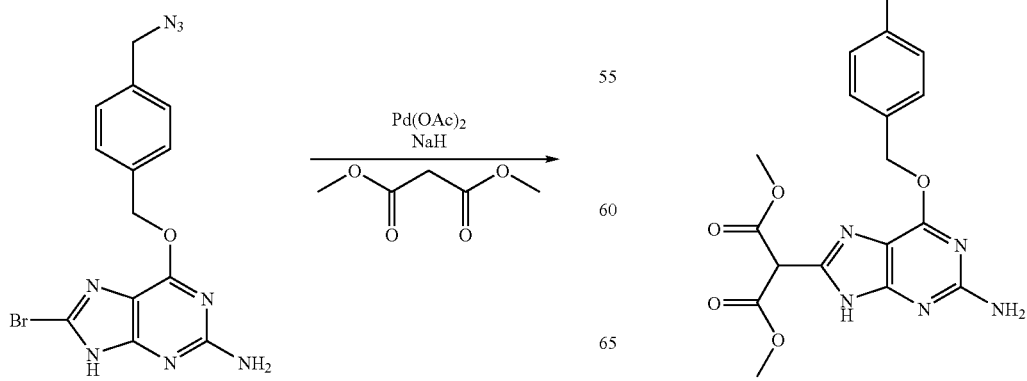

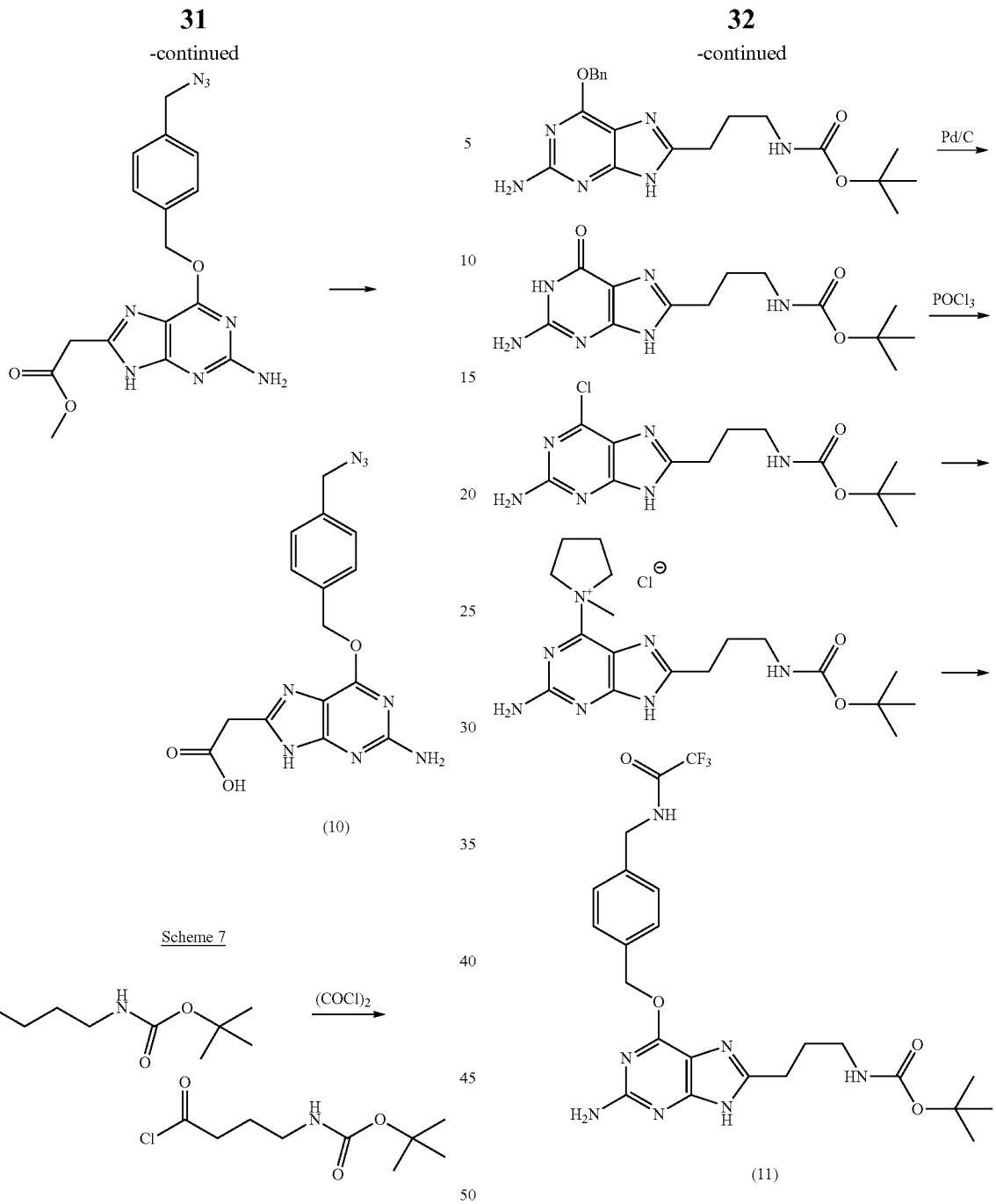

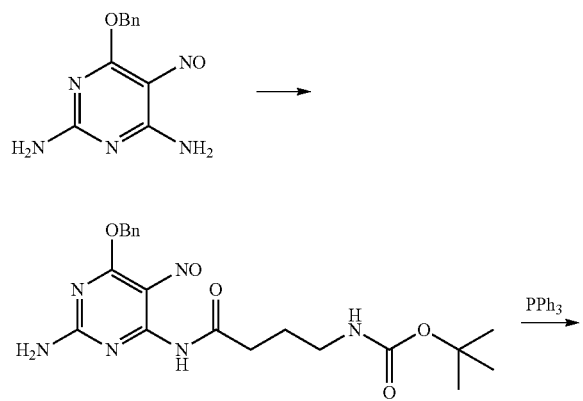

An alternative synthesis of compound of formula (11) is illustrated in Examples 20 to 23. In this alternative synthesis, the p-(trifluoroacetamidomethyl)benzyl substituent is introduced at an earlier stage. The doubly protected compound of formula (11) may then be further elaborated to compounds carrying Labels $L_1$ and $L_2$ in positions $O^6$ and $C^8$, respectively, as described e.g. in Examples 24 to 42.

For the preparation of compounds of formula (1) wherein $R_1$-A is a pyrimidine residue of formula (4a), $R_9$ is amino and $R_{10}$ is nitroso, the sequence of reaction shown in Scheme 8 or 9 is performed. 4-Chloro-2,6-diaminopyrimidine is reacted with the appropriate sodium alkoxide and then treated with sodium nitrite in 30% acetic acid to introduce the nitroso function. $N^6$-substituted derivatives are prepared by treatment with the appropriate anhydride or acyl chloride.

Scheme 8
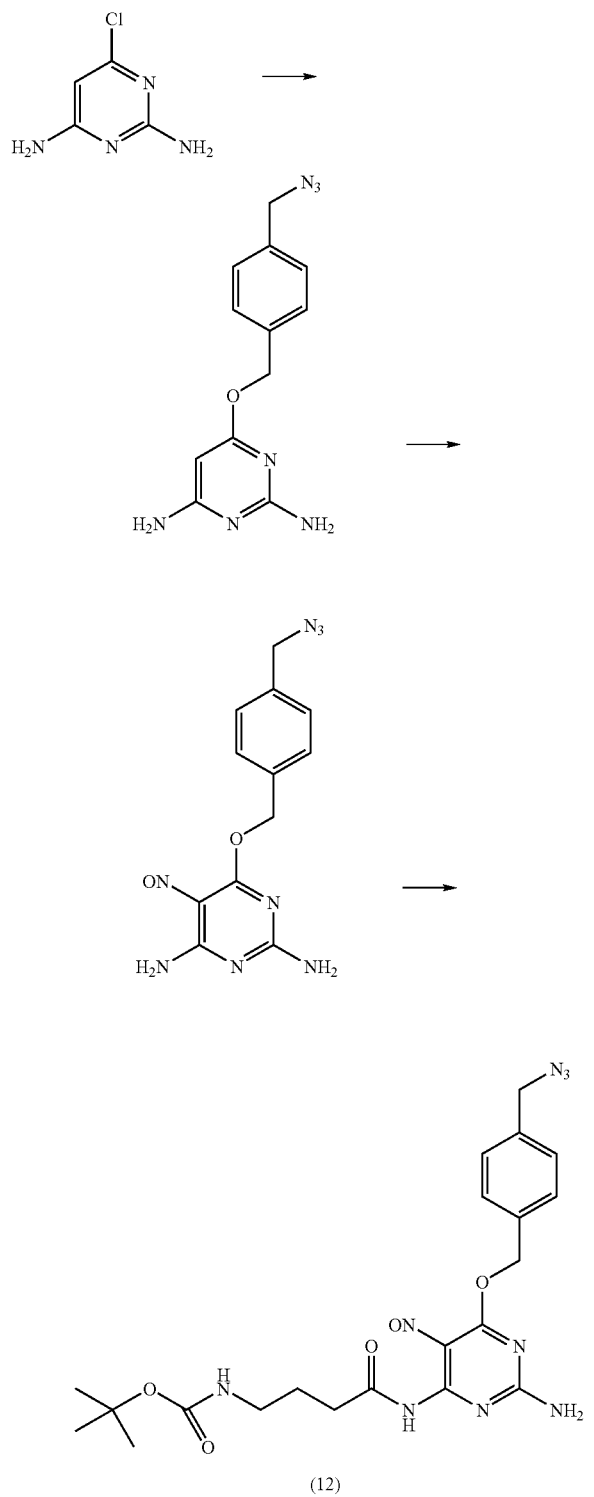
Scheme 9
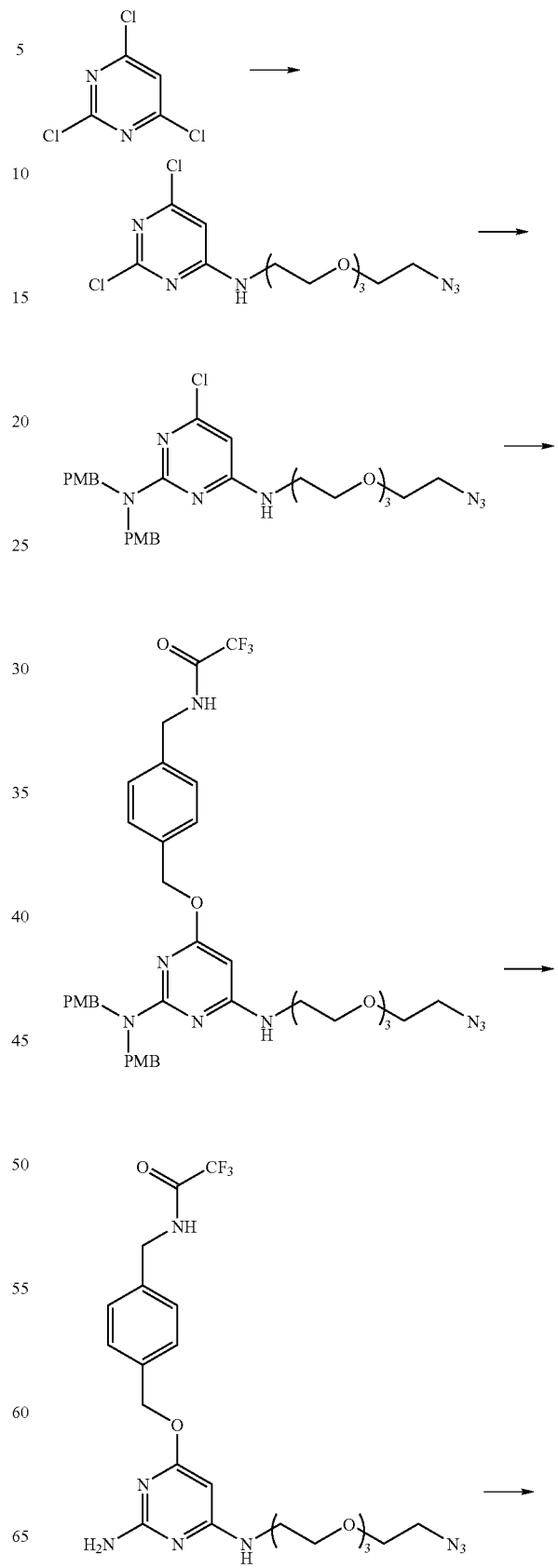
If the immediate precursor of compound (12), a 2,6-diamino-5-nitrosopyrimidine, is reduced to the corresponding 2,5,6-triaminopyrimidine, pteridines of formula (4c) may be obtained through condensation with dihydroxyacetone and further elaboration of the side chain as described in Examples 43 to 46.

-continued (13)

The introduction of an aminoalkyl substituent at the $N^6$ position is shown in Scheme 9. Reaction of 11-azido-3,6,9-trioxa-undeca-amine with 2,4,6-trichloropyrimidine yields the 6-substituted chloropyrimidine accompanied by the 2,6-disubstituted product which can be separated by chromatography. Substitution of the 2-position with bis-p-methoxy-benzylamine (PMB) as a masked ammonia equivalent gives the disubstituted pyrimidine which is subsequently converted into the $O^4$ derivative by reaction with the appropriate alkoxide. Deprotection with trifluoroacetic acid at 60° C. liberates the 2-aminopyrimidine. The 5-nitroso compound is prepared with sodium nitrite in acetic acid.

EXAMPLES

Abbreviations:
DMF=dimethylformamide
DMSO=dimethylsulfoxide
DTT=dithiothreitol
equiv.=equivalents
MPLC=Medium pressure liquid chromatography
sat.=saturated
THF=tetrahydrofuran
TEA=triethylamine
TLC=thin layer chromatography Example 1

(4-Bromothiophen-2-yl)-methanol (14)

NaBH$_4$ (1.11 g, 29.31 mmol) is added to a solution of 4-bromothiophene-2-carbaldehyde (5 g, 26.17 mmol) in isopropanol (70 mL). The reaction mixture is stirred for 2 h at room temperature. A saturated aqueous solution of NH$_4$Cl (15 mL) is added to the solution. The suspension is filtered, the filtrate concentrated in vacuo, dissolved in CH$_2$Cl$_2$ (70 mL), dried over MgSO$_4$ and concentrated in vacuo again. The residue is purified by flash chromatography (ethyl acetate/petrol ether 1:10). Yield 4.55 g (23.55 mmol, 90%). TLC: R$_f$=0.75 (ethyl acetate/petrol ether 1:1). $^1$H NMR (CDCl$_3$): δ=2.07 (br.s, 1H, OH), 4.78 (d, 2H, CCH$_2$OH), 6.92 (s, 1H, CCHC(Br)), 7.17 (s, 1H, C(Br)CHS) ppm.

Example 2

2-Cyclopentenyl methyl carbonate (15)

Methyl chloroformate (2.94 mL, 38 mmol) is added dropwise over 30 min. to a stirred solution of cyclopent-2-en-1-ol (1.0 g, 11.9 mmol, J.-L. Luche, J. Am. Chem. Soc., 1978, 100:7, 2226-2227) in CH$_2$Cl$_2$ (30 mL) and pyridine (10 mL) at 0° C. After 4 h TLC shows complete reaction, and the reaction mixture is poured into sat. NH$_4$Cl (50 mL) and extracted with Et$_2$O (3×50 mL). The organic phase is washed with HCl 1 M until the washings are acidic, washed with water (50 mL), brine (50 mL) and dried over MgSO$_4$. The crude product is purified by flash chromatography (ethyl acetate/petrol ether 1:100). Yield 1.777 g (12.5 mmol, 53%). TLC R$_f$=0.70 (ethyl acetate/petrol ether 1:12). $^1$H NMR (CDCl$_3$): δ=1.88-1.96 (m, 1H, CH$_2$CH$_2$CH(OH) syn), 2.24-2.37 (m, 2H, CHCH$_2$CH$_2$ anti, CH$_2$CH$_2$CH(OH) anti), 2.49-2.59 (m, 1H, CHCH$_2$CH$_2$ syn), 3.77 (s, 3H, OH$_3$), 5.61-5.64 (m, 1H, CH—CH(O)CH$_2$), 5.87-5.89 (m, 1H, CH$_2$CH=CH), 6.13-6.16 (m, 1H, CH=CHCH(O)) ppm.

Example 3

$N^9$-(Cyclopent-2-enyl)-6-chloroguanine (16)

This reaction is performed under anhydrous conditions (argon atmosphere and solvents over molecular sieve). To a solution of 6-chloroguanine (596 mg, 3.52 mmol) in DMSO (10 mL), Pd(PPh$_3$)$_4$ (404 mg, 0.35 mmol) is added followed by a solution of 2-cyclo-pentenyl methyl carbonate (13) (500 mg, 3.52 mmol) in THF (10 mL). The reaction mixture is stirred 1 h at room temperature. It is poured into H$_2$O (60 mL) and extracted with ethyl acetate (3×50 mL). The combined organic layers are washed with brine (60 mL), dried over MgSO$_4$ and concentrated in vacuo. The residue is purified by flash column chromatography (ethyl acetate/petrol ether 6 4). Yield: 381 mg (1.62 mmol, 61%). TLC R$_f$=0.33 (ethyl acetate/petrol ether 6:4). $^1$H NMR (CDCl$_3$): δ=1.88-1.95 (m, 1H, CH$_2$CH$_2$CH(OH) syn), 2.49-2.71 (m, 3H, CHCH$_2$CH$_2$ syn, CHCH$_2$CH$_2$ anti, CH$_2$CH$_2$CH(OH) anti), 5.04 (broad s, 2H, NH$_2$), 5.56-5.60 (m, 1H, CHCH(N)CH$_2$), 5.85-5.88 (m, 1H, CH$_2$CH=CH), 6.29-6.32 (m, 1H, CH=CHCH(N)), 7.72 (s, 1H, NCH=N) ppm.

Example 4

$N^9$-Cyclopentyl-6-chloroguanine (17)

Palladium on active charcoal (100 mg) is added to a solution of $N^9$-(cyclopent-2-enyl)-6-chloroguanine (16) (200 mg, 0.85 mmol) in methanol (33 mL). Hydrogen gas is passed through the solution during 30 min. The crude product is adsorbed on silica (500 mg) and purified by flash chromatography (ethyl acetate/petrol ether 1:4, 3:7 and 2:3). Yield: 111 mg (0.47 mmol, 55%). TLC R$_f$=0.34 (ethyl acetate/petrol ether 1:1).

$^1$H NMR (CDCl$_3$): δ=1.79 (m, 2H, CH$_2$CH$_2$CH(OH) syn), 1.94 (m, 4H, CH$_2$CH$_2$CH$_2$ anti, CH$_2$CH$_2$CH(OH) anti), 2.24 (m, 2H, CH$_2$CH$_2$CH$_2$ syn), 4.77 (qnt, 1H, CH$_2$CH(N)CH$_2$), 5.03 (broad s, 2H, NH$_2$), 7.81 (s, 1H, NCH=N) ppm. $^{13}$C-NMR δ=24.0, 32.6, 56.1, 125.8, 140.8, 151.3, 153.9, 158.9 ppm. MS (ESI) m/z 238.28.

Alternatively, cyclopentyl bromide (200 mg, 1.34 mmol) is added to a suspension of 6-chloroguanine in dimethylacetamide, followed by NaOMe (144 mg, 2.67 mmol). The solution is stirred over night at 100° C. The solvents are evaporated in vacuo. The residue is adsorbed on silica (1 g) and purified by flash chromatography (ethyl acetate/petrol ether 1:1). Yield: 140 mg (0.59 mmol, 44%).

Example 5

$N^9$-Cyclopentyl-$O^6$-(4-bromothiophen-2-yl)-guanine (CPTG, 18)

To a solution of $N^9$-cyclopentyl-6-chloroguanine (17, 50 mg, 0.21 mmol) in DMF (1.3 mL) 1,4-diazabicyclo[2.2.2]octane (DABCO, 71 mg, 0.63 mmol) is added. The reaction mixture is stirred 3 h at room temperature. TLC shows complete reaction. A solution of (4-bromothiophen-2-yl)-methanol (14, 49 mg, 0.25 mmol) and 1,8-diazabicyclo[5.4.0]-undec-7-ene (DBU) (96 mg, 0.094 mL, 0.63 mmol) in DMF (0.7 mL) is then added to the reaction mixture. The solution is stirred over night at room temperature. The crude product is purified by flash chromatography (ethyl acetate/petrol ether 1:9→3:7). Yield 25 mg (0.063 mmol, 30%). TLC $R_f$=0.23 (ethyl acetate/petrol ether 1:1).

$^1$H NMR (CDCl$_3$): δ=1.77 (m, 2H, CH$_2$CH$_2$CH(OH) syn), 1.92 (m, 4H, CH$_2$CH$_2$CH$_2$ anti, CH$_2$CH$_2$CH(OH) anti), 2.21 (m, 2H, CH$_2$CH$_2$CH$_2$ syn), 4.76 (qnt, 1H, CH$_2$CH(N)CH$_2$), 4.87 (broad s, 2H, NH$_2$), 5.64 (s, 2H, OCH$_2$C), 7.11 (s, 1H, C═CHC(Br)), 7.18 (s, 1H, C(Br)CHS), 7.66 (s, 1H, NCHN) ppm. $^{13}$C-NMR δ=24.0, 32.8, 55.7, 61.8, 109.2, 116.0, 124.1, 131.0, 138.0, 140.1, 154.6, 158.7, 160.3 ppm. MS (ESI) m/z 394.36.

Example 6

$N^9$-Benzyl-6-chloroguanine (19)

A flask is charged with 6-chloroguanine, PPh$_3$ and benzyl alcohol. The mixture is dried in vacuo for 3 h and subsequently dissolved in dry THF to which activated molecular sieves (4 Å) are added. After stirring for 15 min diisopropyl azodicarboxylate (DIAD) is added. The reaction is stirred over night. Solvent is removed under reduced pressure, and the product is purified via column chromatography (petrol ether/ethyl acetate 3:1). $^1$H-NMR: δ=7.65-7.26 (m, 6H), 5.25 (s, 2H), 5.10 (s, br, 2H); UV: λ$_{max}$: 306 nm.

Example 7

$N^9$-Benzyl-$O^6$-(4-bromothiophen-2-yl)-guanine (20)

To a solution of $N^9$-benzyl-6-chloroguanine (19, 50 mg, 0.19 mmol) in DMF (1.5 mL) 1,4-diazabicyclo[2.2.2]octane (DABCO, 65 mg, 0.57 mmol) is added. The reaction mixture is stirred 3 h at room temperature. TLC shows complete reaction. A solution of (4-bromo-thiophen-2-yl)-methanol (14, 44 mg, 0.23 mmol) and 1,8-diazabicyclo[5.4.0]-undec-7-ene (DBU) (88 mg, 0.086 mL, 0.57 mmol) in DMF (0.7 mL) is then added to the reaction mixture. The solution is stirred over night at room temperature. The crude product is purified by flash chromatography (ethyl acetate/petrol ether 1:4→3:7) Yield 27 mg (0.065 mmol, 34%). TLC $R_f$=0.20 (ethyl acetate/petrol ether 1:1). $^1$H NMR (CDCl$_3$): δ=4.88 (broad s, 2H, NH$_2$), 5.23 (s, 2H, NCH$_2$C), 5.65 (s, 2H, OCH$_2$C), 7.12 (s, 1H, C═CHC(Br)), 7.19 (s, 1H, C(Br)CHS), 7.24-7.71 (m, 5H, arom.), 7.56 (s, 1H, NCHN) ppm. MS (ESI) m/z 416.33.

Example 8

$N^9$-(3-Chloropropyl)-2-amino-6-chlorpurine (21)

To a stirred suspension of 6-chloropurine (5.0 g, 29.48 mmol) and K$_2$CO$_3$ (4.48 g, 32.42 mmol) in dry DMF 1-bromo-3-chloropropane (13.92 g, 88.45 mmol) is added. The reaction mixture is heated to 50° C. for 1 min and stirred at room temperature for additional 3 h. The reaction mixture is poured into 120 mL of water and extracted with CH$_2$Cl$_2$. The combined organic phases are washed with water, dried over MgSO$_4$ and evaporated in vacuo. The residue is purified by flash column chromatography (dichloromethane/methanol 50:1 to 10:1) to yield 2.6 g (10.65 mmol, 35%) of the title compound as a colorless solid. $^1$H-NMR (400 MHz, DMSO-d$_6$): δ=8.11 (s, 1H, H-8), 6.91 (s, 2H, NH$_2$), 4.16 (t, J=6.8, 2H, CH$_2$), 3.63 (t, J=6.8, 2H CH$_2$), 2.25 (m, 2H, CH$_2$) ppm. MS (ESI) m/z 247.3 [M+H]$^+$.

Example 9

$N^9$-(3-Azidopropyl)-2-amino-6-chlorpurine (22)

$N^9$-(3-Chloropropyl)-2-amino-6-chlorpurine (21, 2.56 g, 10.40 mmol) and sodium azide (811 mg, 12.48 mmol) are dissolved in 25 mL DMSO and stirred at 80° C. for 16 h. After cooling to room temperature, the reaction mixture is poured into 150 mL of water and extracted with CH$_2$Cl$_2$. The combined organic phases are washed with water, dried over MgSO$_4$ and evaporated in vacuo. The residue is purified by flash column chromatography (dichloromethane/methanol 50:1 to 10:1) to yield the title compound as a colorless solid (650 mg, 2.57 mmol, 24%). $^1$H-NMR (400 MHz, DMSO-d$_6$): δ=8.12 (s, 1H, H-8), 6.89 (s, 2H, NH$_2$), 4.10 (t, J=6.8, 2H, CH$_2$), 3.38 (t, J=6.8, 2H, CH$_2$), 2.05 (m, 2H, CH$_2$) ppm. MS (ESI) m/z 253.0 [M+H]$^+$.

Example 10

N-[4-(2-Amino-9-(3-azidopropyl)-purine-6-yloxymethyl)-benzyl]-2,2,2-trifluoro-acetamide (23)

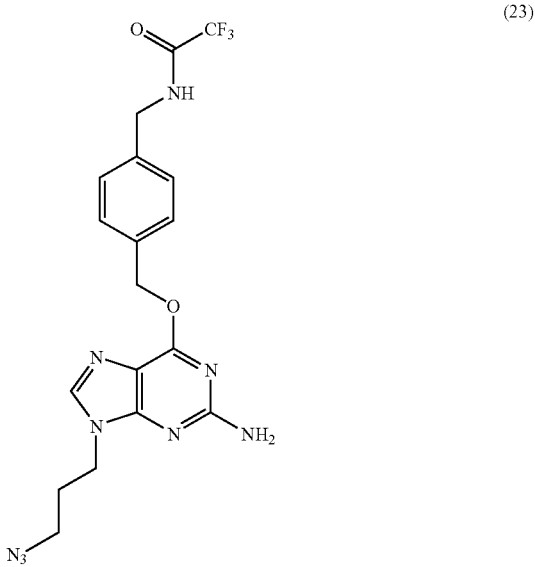

2,2,2-Trifluoro-N-(4-hydroxymethyl-benzyl)-acetamide (138 mg, 0.59 mmol) is dissolved in 3 mL dry dimethylacetamide under argon atmosphere, and (31 mg, 1.31 mmol) NaH is added. $N^9$-(3-Azidopropyl)-2-amino-6-chloropurine (22, 100 mg, 0.39 mmol) is added and the solution heated to 90° C. for 16 h. After cooling to room temperature, the mixture is poured into 80 mL of water and the pH is adjusted to 6 with trifluoroacetic acid. The aqueous phase is extracted with $CH_2Cl_2$ and ethyl acetate. The organic phases are washed with water and brine, dried over $MgSO_4$ and the solvent is evaporated. The crude product is dissolved in methanol, adsorbed on $SiO_2$ (150 mg) and purified by flash column chromatography with dichloromethane:methanol (95:5). Yield: 151 mg (0.0336 mmol, 85%). $^1$H-NMR (400 MHz, DMSO-$d_6$): δ=10.00 (t, J=5.8, 1H, $CF_3$CONH), 7.90 (s, 1H, H-8), 7.49, (d, J=8.1, 2H, ArH), 7.28 (d, J=8.1, 2H, ArH), 6.47 (s br, 2H, $NH_2$), 5.46 (s, 2H, $OCH_2$), 4.38 (d, J=5.8, 2H, C$H_2$NH), 4.06 (t, J=6.5, 2H, $CH_2$), 3.36 (t, J=6.5, 2H, $CH_2$), 2.00 (m, 2H, $CH_2$) ppm. MS (ESI) m/z 450.0 $[M+H]^+$.

Example 11

N-[4-(2-Amino-9-(3-aminopropyl)-purine-6-yloxymethyl)-benzyl]-2,2,2-trifluoro-acetamide (24)

Azide 23 (Example 10, 100 mg, 0.23 mmol) is dissolved in 0.9 mL of 1,4-dioxane/$H_2O$ (8:1), and 0.3 mL of a trimethylphospine solution (1 M in THF) is added. The reaction is stirred at room temperature for 3 h, then all volatiles are removed in vacuo. The crude product is purified by flash column chromatography with dichloromethane/methanol (95:5 to 10:1). Yield: 87 mg (0.021 mmol, 91%).

Example 12

N-[4-(2-Amino-9-(3-(4-[4-dimethylamino-phenyl]-azo-benzoyl)-amino-propyl)-purine-6-yloxymethyl)-benzyl]-2,2,2-trifluoro-acetamide (25)

4-([4-Dimethylamino-phenyl]-azo)-benzoic acid succinimidyl ester (14.3 mg, 0.0039 mmol) and trifluoroacetamide 24 (Example 11, 16.6 mg, 0.0039 mmol) are dissolved in 0.8 mL DMF with 10 µL TEA. The reaction mixture is stirred at room temperature over night and the product purified via reversed phase MPLC.

Example 13

4-(2-Amino-9-(3-(4-[4-dimethylamino-phenyl]-azo-benzoyl)-aminopropyl)-purine-6-yloxymethyl)-benzylamine (26)

Trifluoroacetamide 25 (Example 12, 50 mg) is dissolved in 1 mL methanol, and 2 mL methylamine (33% in ethanol) are added. The reaction mixture is stirred at room temperature over night and all volatiles are removed in vacuo. The product is used without further purification in the next step. MS (ESI) m/z 579.1 $[M+H]^+$.

Example 14

N-[4-(2-Amino-9-(3-(4-[4-dimethylamino-phenyl]-azo-benzoyl)-amino-propyl)-purine-6-yloxymethyl)-benzyl]-ATTO488-amide (27)

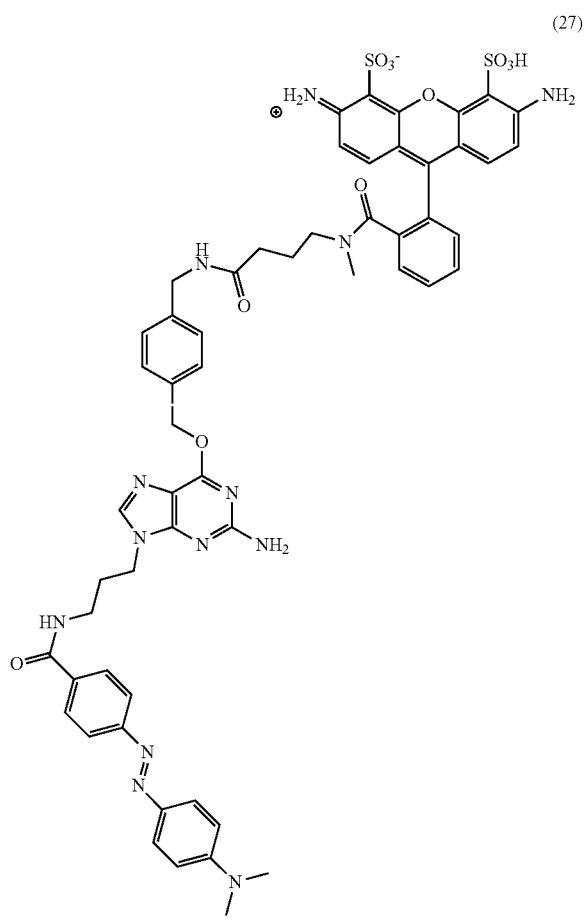

(27)

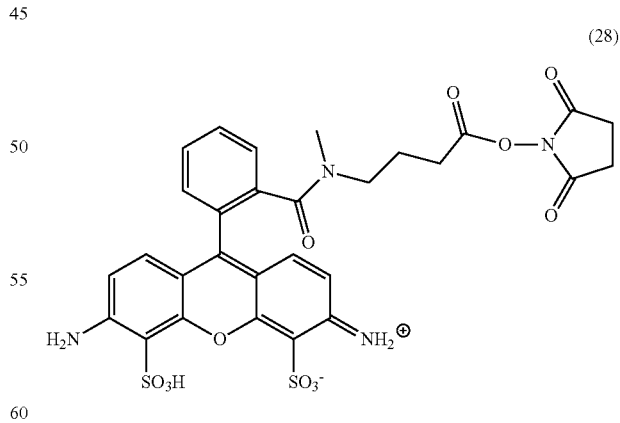

(28)

Amine 26 (Example 13, 2 mg) and ATTO 488-succinimidyl ester (28, 2 mg, Atto-Tech, Siegen, Germany, Cat.-No. AD488-3) are dissolved in 150 µL DMF with 1 µL TEA and left at room temperature for 24 h. The product (27) is purified by reversed phase MPLC.

Example 15

N-[4-(2-Amino-9-(3-(4-[4-dimethylamino-phenyl]-azo-benzoyl)-amino-propyl)-purine-6-yloxymethyl)-benzyl]-fluoresceine-5(6)-carboxamide (29)

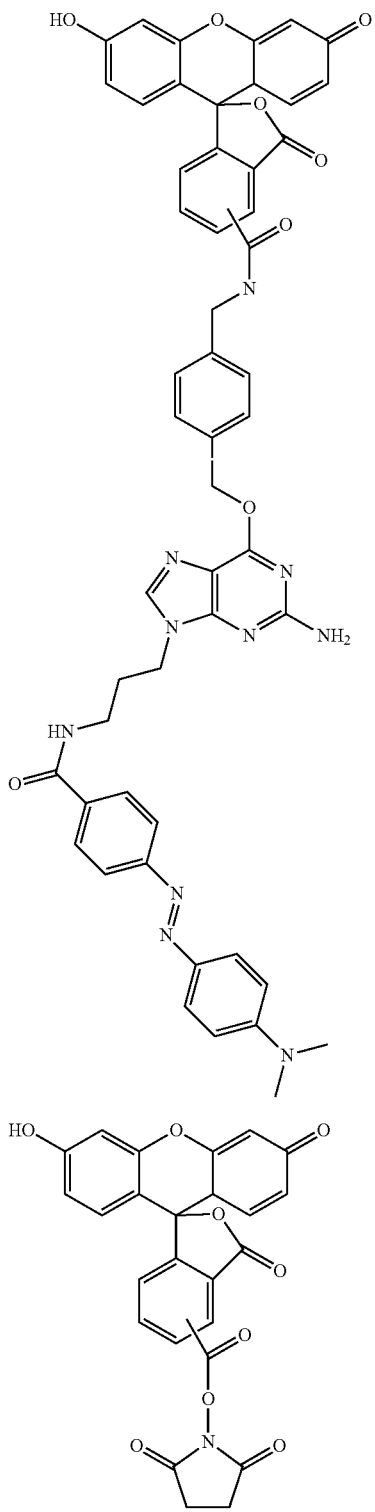

Amine 26 (Example 13, 2 mg, 0.0034 mmol) and 5(6)-carboxyfluoresceine succinimidyl ester (30, 2.0 mg, 0.0042 mmol) are dissolved in 150 μL DMF with 1 μL TEA and left at room temperature for 24 h. The product (29) is purified by reversed phase MPLC.

Example 16

4-(2-Amino-9-(3-azidopropyl)-purin-6-yloxymethyl)-benzylamine (31)

Azide 23 (Example 10, 50 mg, 0.11 mmol) is dissolved in 1 mL methanol, and 2 mL methylamine (33% in ethanol) are added. The reaction mixture is stirred at 50° C. over night and all volatiles are removed in vacuo. The product is purified by flash column chromatography ($CH_2Cl_2$/MeOH 10:1) to yield 33.5 mg. $^1$H-NMR (400 MHz, DMSO-$d_6$): δ=7.85 (s, 1H, H-8), 7.41, (d, J=8.1, 2H, ArH), 7.35 (d, J=8.1, 2H, ArH), 6.44 (s br, 2H, $NH_2$), 5.44 (s, 2H, $OCH_2$), 4.05 (t, J=, 2H, $CH_2$), 3.72 (s, 2H, $CH_2$), 3.35 (t, J=6.5, 2H, $CH_2$), 1.99 (m, 2H, $CH_2$) ppm. MS (ESI) m/z 354.1 $[M+H]^+$.

Example 17

N-[4-(2-Amino-9-(3-azidopropyl)-purin-6-yloxymethyl)-benzyl]-tetramethyl-rhodamine-5(6)-carboxamide (32)

Azide 31 (Example 16, 10 mg, 0.08 mmol) and 5(6)-carboxytetramethylrhodamine succinimidyl ester (33, 7.47 mg, 0.014 mmol) are dissolved in 850 μL DMF with 20 μL TEA and left at room temperature for 24 h. The product is purified by reversed phase MPLC to yield 9.0 mg (0.012 mmol, 79%). MS (ESI) m/z 766.0 $[M]^+$.

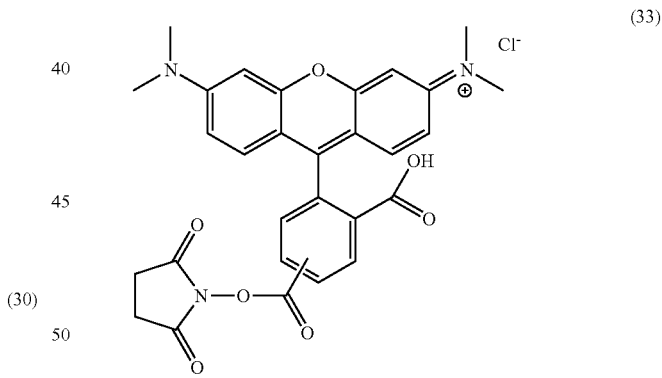

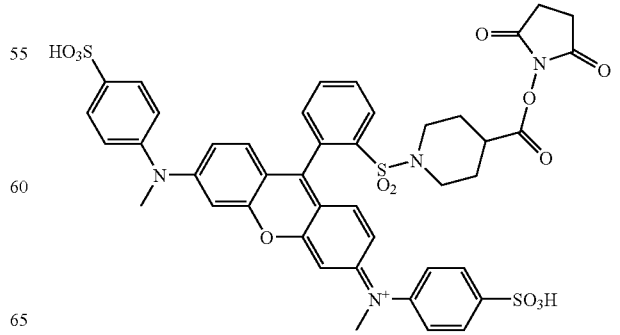

Example 18

N-[4-(2-Amino-9-(3-aminopropyl)-purin-6-yloxymethyl)-benzyl]-tetramethyl-rhodamine-5(6)-carboxamide (34)

Azide 32 (Example 17, 9.0 mg, 0.012 mmol) is dissolved in a mixture of 600 μL 1,4-dioxane and 80 μL water. From this stock solution, 200 μL are treated with a solution of 14 μL trimethylphosphine (1 M in THF) for 3 h. All volatiles are removed in vacuo and the product is purified by reverse phase MPLC by using a linear gradient from water to acetonitrile (0.08% TFA). Yield 3.47 mg (0.0047 mmol, 40%). MS (ESI) m/z 740.1 [M+].

Example 19

N-[4-(2-Amino-9-(3-QSY9-aminopropyl)-purin-6-yloxymethyl)-benzyl]-tetramethylrhodamine-5(6)-carboxamide (35)

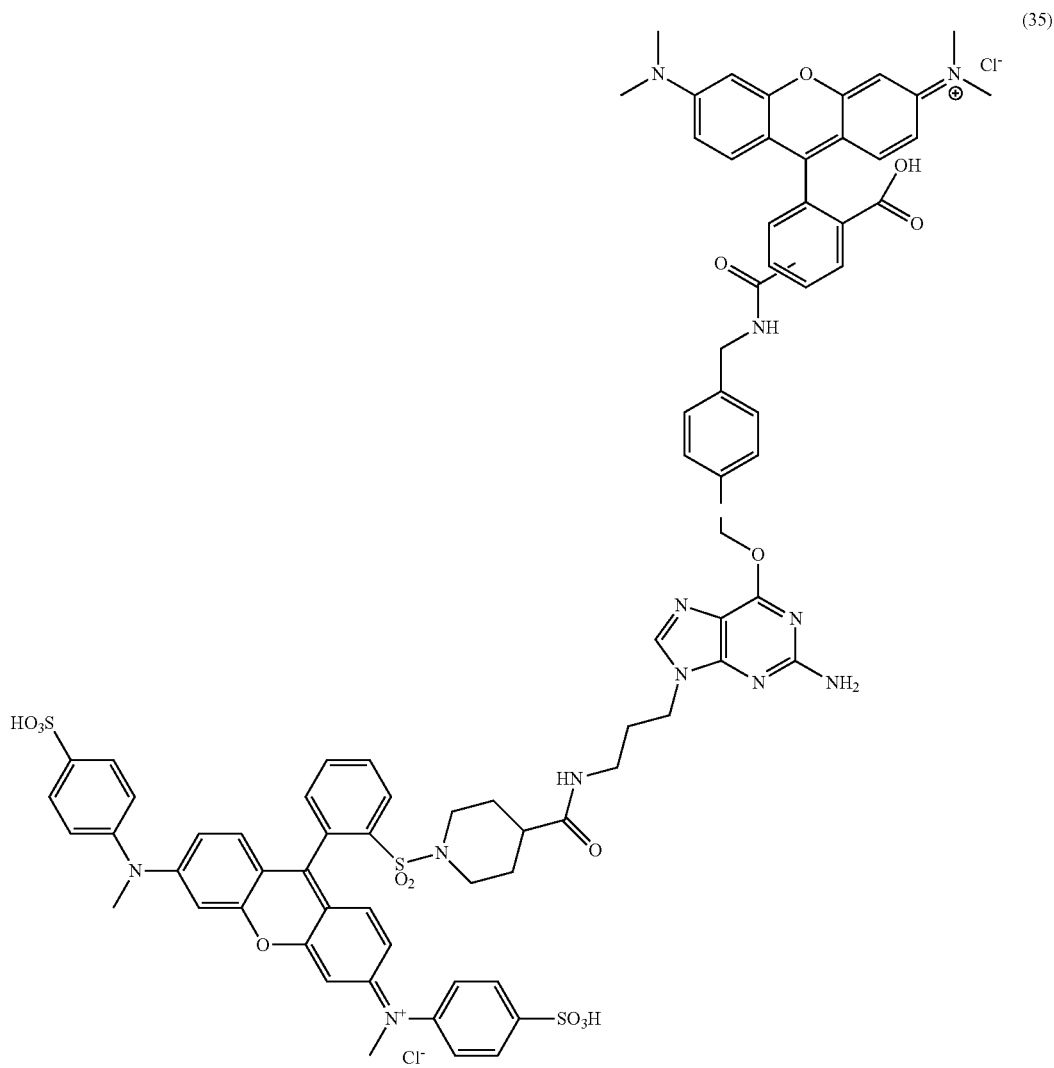

(35)

To a solution of amine 34 (Example 18, 100 μL, 4.7 mM in DMF) QSY-9-succinimidyl ester (36, Molecular Probes, Eugene, Oreg., USA, Cat.-No. Q20131) (0.8 mg) and 1 μL TEA are added and the mixture left on a shaker at room temperature over night. The product is purified by reverse phase MPLC by using a linear gradient from water to acetonitrile (0.08% TFA). MS (ESI) m/z 1539.9 [M+H]$^+$.

Example 20

2,6-Diamino-4-[4-(2,2,2-trifluoro-acetamidomethyl)-benzyloxy]-pyrimidine (37)

N-(4-Hydroxymethyl-benzyl)-2,2,2-trifluoro-acetamide (12.0 g, 52 mmol) is dissolved in 80 ml dry DMSO, and NaH (4.08 g, 102 mmol, suspension 60% in mineral oil) is added in portions over 30 min under an argon atmosphere. After stirring at room temperature for 1 h, 2,6-diamino-4-chloropyrimidine (7.52 g, 52 mmol) is added and the reaction mixture heated to 60° C. over night. After cooling to room temperature, the mixture is poured into 1 L of 1 N HCl, and the product extracted with ethyl acetate (500 mL). The combined organic phases are washed with water and brine, dried over MgSO$_4$, and the solvent evaporated. The residue is purified by flash column chromatography (ethyl acetate/methanol 100:0 to 80:20) to yield the title compound as a colorless solid (4.7 g, 13.78 mmol, 27%). $^1$H-NMR (400 MHz, DMSO-d$_6$): δ=9.99 (t, J=6.1, 1H, CONH), 7.34 (d, J=8.1, 2H, ArH), 7.26 (d, J=8.1, 2H, ArH), 6.02 (s br, 2H, NH2), 5.89 (s br, 2H, NH$_2$), 5.16 (s, 2H, OCH$_2$), 5.01 (s, 1H, 4-H), 4.36 (d, J=6.1, 2H, CH$_2$NCO) ppm.

Example 21

2,6-Diamino-5-nitroso-4-[4-(2,2,2-trifluoro-acetamidomethyl)-benzyloxy]-pyrimidine (38)

Pyrimidine 37 (Example 20, 4.72 g, 13.7 mmol) is dissolved in 60 mL acetic acid (30%) and heated to 70° C. NaNO$_2$ (1.4 g, 20.03 mmol) dissolved in 5 mL water is added drop wise until KJ-starch paper remains black. After cooling to 0° C. in an ice-bath, the purple precipitate is collected by filtration and recrystallized from acetone to yield 3.9 g (10.54 mmol, 77%) of a purple solid. $^1$H-NMR (400 MHz, DMSO-d$_6$) δ=10.03 (d, J=4.0, 1H, 5-NH$_a$), 10.00 (t, J=5.8, 1H, CF$_3$CONH), 8.01 (d, J=4.0, 1H, 5-NH$_b$), 7.86 (s, 1H, 1-NH$_a$), 7.81 (s, 1H, 1-NH$_b$), 7.51 (d, J=8.1, 2H, ArH), 7.30 (d, J=8.1, 2H, ArH), 5.54 (s, 2H, OCH$_2$), 4.38 (d, J=5.8, 2H, CH$_2$N) ppm.

Example 22

2-Amino-6-(4-(tert-butoxycarbonylamino)-butanoylamino)-5-nitroso-4-[4-(2,2,2-trifluoro-acetamidomethyl)-benzyloxy]-pyrimidine (39)

Under an argon atmosphere 4-(tert-butoxycarbonylamino)-butyric acid (1.58 g, 8 mmol) is dissolved in 20 mL dry THF and cooled to 0° C. Diisopropyl ethylamine (1.18 g, 9 mmol) is added, the mixture cooled to −20° C., and chloroformic acid isobutylester (1.15 g, 8 mmol) added. The mixture is stirred at this temperature for 5 min, and nitroso-pyrimidine 38 (Example 21, 2.64 g, 7 mmol) dissolved in 20 mL dry THF is added via a syringe. The reaction mixture is allowed to warm to room temperature, heated to 55° C. and stirred at this temperature over night. After cooling to room temperature, the mixture is poured into 100 mL of 1 N HCl and the product extracted with ethyl acetate (300 mL). The combined organic phases are washed with water and brine, subsequently dried over MgSO$_4$ and the solvent evaporated. The residue is adsorbed on SiO$_2$ and purified by flash column chromatography (cyclohexane/ethyl acetate 1:2 to 1:10) to yield the title compound as a blue solid (1.96 g, 3.53 mmol, 50.4%). From the crude material, an analytical sample is recrystallized from ethyl acetate.

Example 23

N-[4-(2-Amino-8-(3-(tert-butoxycarbonylamino)-propyl)-9H-purin-6-yloxymethyl)-benzyl]-2,2,2-trifluoro-acetamide (11)    (11)

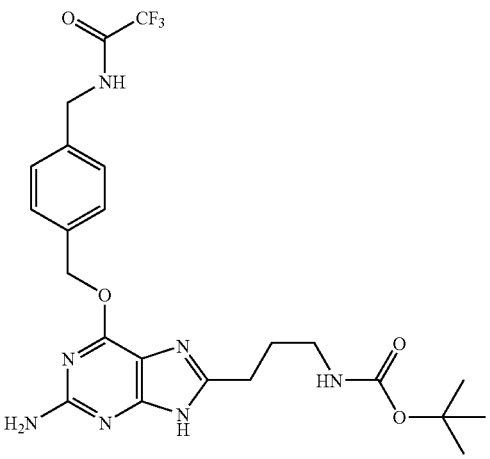

Nitroso-pyrimidine 39 (Example 22, 1.84 g, 3.3 mmol) and triphenylphosphine (1.89 g, 7 mmol) in 20 mL o-xylene are heated to reflux for 10 h. After cooling to room temperature the solvent is removed in vacuo and the remaining residue redissolved in ethyl acetate. The residue is adsorbed on SiO$_2$ and purified by flash column chromatography (ethyl acetate/ethanol 1:0 to 10:1) to yield the title compound as a colorless solid (1.04 g, 3.53 mmol, 50.4%). $^1$H-NMR (400 MHz, DMSO-d$_6$): δ=7.46 (d, J=8.1, 2H, ArH), 7.28 (d, J=8.1, 2H, ArH), 6.85 (t, J=5.3, 1H, CONH), 6.41 (s, 2H, NH$_2$), 5.41 (s, 2H, OCH$_2$), 4.38 (s, 2H, CH$_2$), 2.93 (q, J=6.5, 2H, CH$_2$), 2.60 (t, J=7.1, 2H, CH$_2$), 1.76 (qt, J=7.1; 2H, CH$_2$), 1.35 (s, 9H, (CH$_3$)$_3$) ppm. MS (ESI) m/z 524.3 [M+H]$^+$.

Example 24

N-[4-(2-Amino-8-(3-aminopropyl)-9H-purin-6-yloxymethyl)-benzyl]-2,2,2-trifluoro-acetamide (41)

The tert-butoxycarbonyl derivative 11 (Example 23, 100 mg, 0.19 mmol) is suspended in 10 mL dichloromethane, and 2 mL trifluoroacetic acid are added. The mixture is stirred at room temperature for 30 min and poured into 70 mL of diethyl ether. The precipitate is collected by filtration and purified by flash column chromatography (CH$_2$Cl$_2$/MeOH 5:1) yielding 74 mg (0.17 mmol, 92%) of the title compound. MS (ESI) m/z 424.1 [M+H]$^+$.

Example 25

N-[4-(2-Amino-8-(3-(4-[4-dimethylamino-phenyl]-azo-benzoyl)-amino-propyl)-9H-purin-6-yloxymethyl)-benzyl]-2,2,2-trifluoro-acetamide (42)

Amine 41 (Example 24, 20 mg, 0.047 mmol) and 4-([4-dimethylamino-phenyl]-azo)-benzoic acid succinimidyl ester (17.3 mg, 0.047 mmol) are dissolved in 0.6 mL DMF with 20 μL TEA. The reaction mixture is stirred at room temperature over night and the solvent removed in vacuo. The product is purified by flash column chromatography ($CH_2Cl_2$/MeOH 95:5 to 10:1) yielding 23 mg (0.035 mmol, 75%). MS (ESI) m/z 675.1 $[M+H]^+$.

Example 26

4-(2-Amino-8-(3-(4-[4-dimethylamino-phenyl]-azo-benzoyl)-aminopropyl)-9H-purin-6-yloxymethyl)-benzyl-amine (43)

Trifluoroacetamide 42 (Example 25, 23 mg, 0.035 mmol) is dissolved in 2 mL methanol, and 2 mL methylamine (33% in ethanol) are added. The reaction mixture is stirred at 50° C. over night and all volatiles are removed in vacuo. The product is used without further purification. MS (ESI) m/z 579.1 $[M+H]^+$.

Example 27

N-[4-(2-Amino-8-(3-(4-[4-dimethylamino-phenyl]-azo-benzoyl)-amino-propyl)-9H-purin-6-yloxym-ethyl)-benzyl]-fluoresceine-5(6)-carboxamide (44)

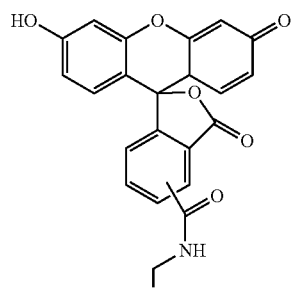
(44)

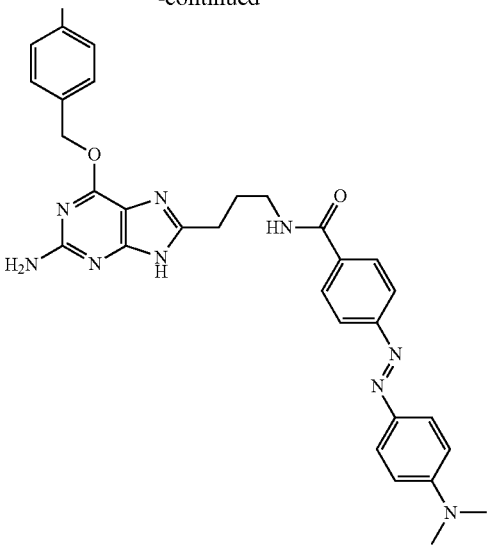

Amine 43 (Example 26, 2.0 mg, 0.0035 mmol) and 5-(6)-carboxyfluoresceine succinimidyl ester (1.63 mg, 0.0035 mmol) are dissolved in 200 μL DMF with 5 μL TEA. The reaction mixture is left at room temperature over night and the crude product is purified by reverse phase MPLC by using a linear gradient from water to acetonitrile (0.08% TFA). MS (ESI) m/z 937.0 $[M+H]^+$.

Example 28

N-[4-(2-Amino-8-(3-(4-[4-dimethylamino-phenyl]-azo-benzoyl)-aminopropyl)-9H-purin-6-yloxym-ethyl)-benzyl]-ATTO488-amide (45)

(45)

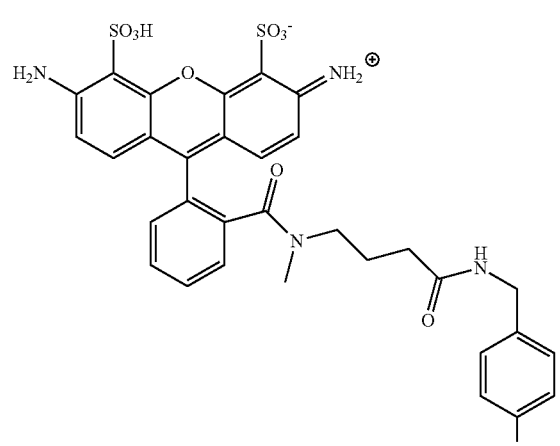

-continued

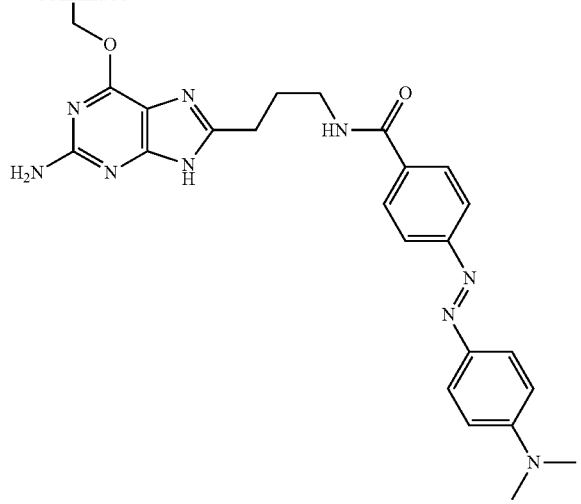

Amine 43 (Example 26, 1.0 mg, 0.0017 mmol) and ATTO488-succinimidyl ester (28, 1.0 mg, 0.0015 mmol) are dissolved in 100 μL DMF with 1 μL TEA. The reaction mixture is left at room temperature over night and the crude product is purified by reverse phase MPLC by using a linear gradient from water to acetonitrile (0.08% TFA). MS (ESI) m/z 1150.0 [M+].

Example 29

N-[4-(2-Amino-8-(3-QSY9-aminopropyl)-9H-purin-6-yloxymethyl)-benzyl]-2,2,2-trifluoro-acetamide (46)

Amine 41 (Example 24, 1.6 mg, 0.038 mmol) and QSY-9-succinimidyl ester (36, 3.7 mg, 0.038 mmol) are dissolved in 0.25 mL DMF with 2 μL TEA. The reaction mixture is stirred at room temperature over night. The reaction mixture is diluted with 1 mL water/acetonitrile (80:20), and the product purified by reversed phase MPLC using a linear gradient from water to acetonitrile (0.08% TFA) yielding 2.1 mg (0.0017 mmol, 44%) of the title compound.

Example 30

4-(2-Amino-8-(3-QSY9-aminopropyl)-9H-purin-6-yloxymethyl)-benzyl-amine (47)

Trifluoroacetamide 46 (Example 29, 2.1 mg, 1.72 μmol) are dissolved in 1 mL methanol, and 2 mL methylamine (33% in ethanol) are added. The reaction mixture is stirred at room temperature over night and all volatiles are removed in vacuo. The product is used without further purification.

Example 31

N-[4-(2-Amino-8-(3-QSY9-aminopropyl)-9H-purin-6-yloxymethyl)-benzyl]-tetramethylrhodamine-5(6)-carboxamide (48)

(48)

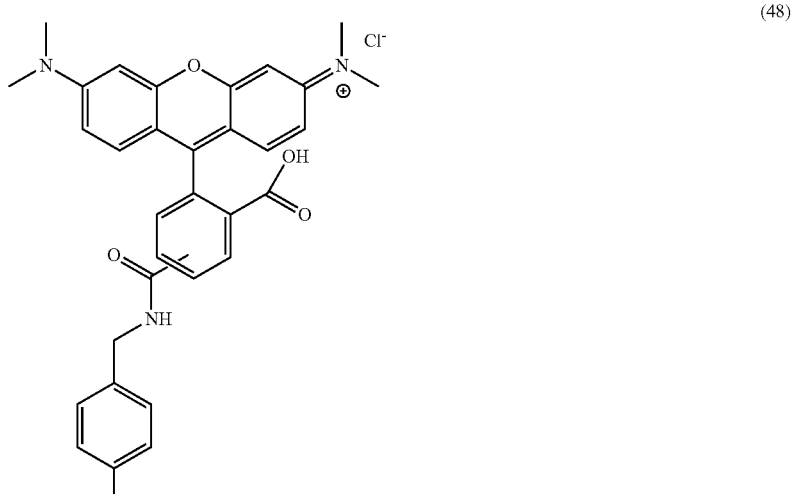

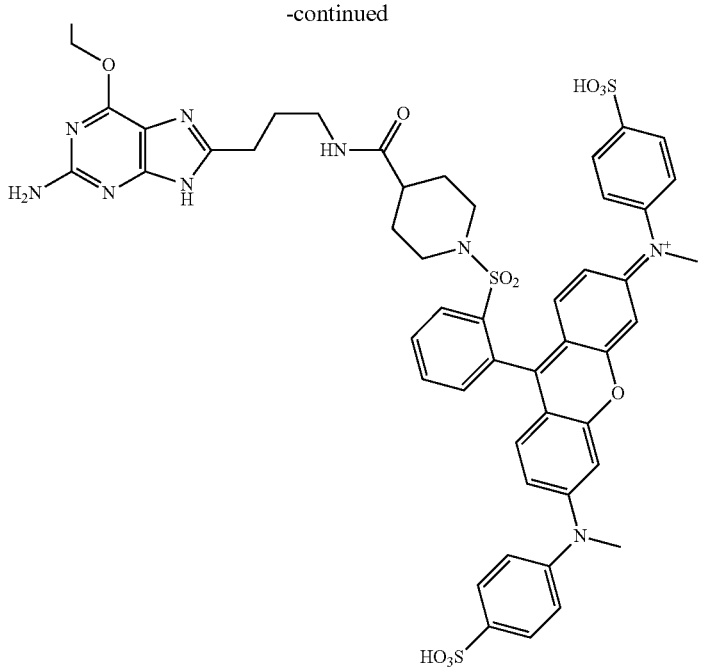

Amine 47 (Example 30, 1 mg, 0.886 µmol), 5(6)-carboxytetramethylrhodamine succinimidyl ester (33, 0.5 mg, 0.886 µmol) and 1 µL TEA are dissolved in 100 µL DMF, and the mixture is left on a shaker at room temperature over night. The product is purified by reverse phase MPLC by using a linear gradient from water to acetonitrile (0.08% TFA).

Example 32

N-[4-(2-Amino-8-(3-(N-(+)-biotinyl-6-aminocaproyl)-aminopropyl)-9H-purine-6-yloxymethyl)-benzyl]-2,2,2-trifluoro-acetamide (49)

Amine 41 (Example 24, 10 mg, 0.023 mmol) and N-(+)-biotinyl-6-aminocaproic acid succinimidyl ester (50, 10 mg, 0.023 mmol) are dissolved in 650 µL DMF with 5 µL TEA and left at room temperature over night. The product is purified by reverse phase MPLC by using a linear gradient from water to acetonitrile (0.08% TFA) to yield 15.1 mg (0.019 mmol, 86%) of the title compound. MS (ESI) m/z 763.0 [M+H]$^+$.

Example 33

4-(2-Amino-8-(3-(N-(+)-biotinyl-6-aminocaproyl)-aminopropyl)-9H-purin-6-yloxymethyl)-benzylamine (51)

Trifluoroacetamide 49 (Example 32, 15.1 mg, 0.019 mmol) are dissolved in 1 mL methanol, and 2 mL methylamine (33% in ethanol) are added. The reaction mixture is stirred at room temperature for 48 h and all volatiles are removed in vacuo. The product is used without further purification. MS (ESI) m/z 667.5 [M+H]$^+$.

Example 34

N-[4-(2-Amino-8-(3-(N-(+)-biotinyl-6-aminocaproyl)-aminopropyl)-9H-purin-6-yloxymethyl)-benzyl]-fluoresceine-5(6)-carboxamide (52)

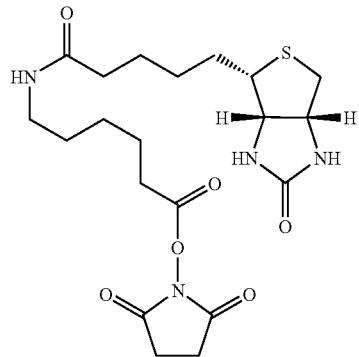

(50)

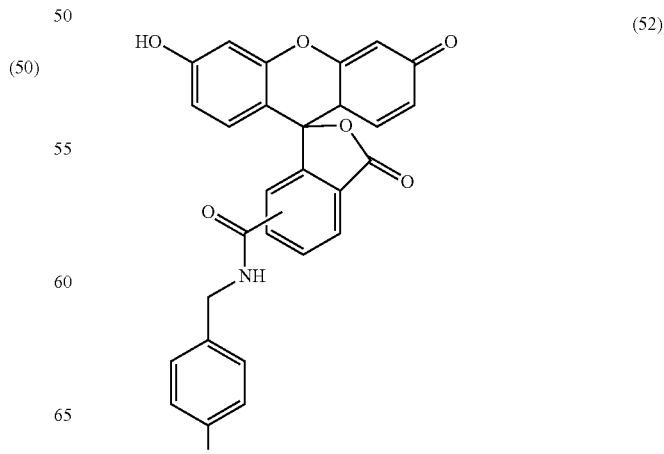

(52)

53

-continued

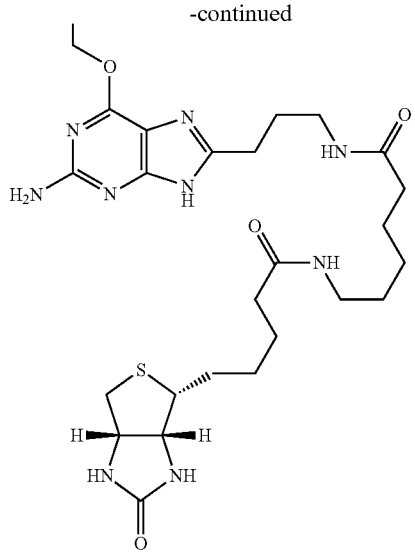

Amine 51 (Example 33, 10 mg, 0.015 mmol) and 5(6)-carboxyfluoresceine succinimidyl ester (30, 7.0 mg, 0.015 mmol) are dissolved in 500 µL DMF with 10 µL TEA. The reaction is left at room temperature for 24 h and the product is purified by reverse phase MPLC by using a linear gradient from water to acetonitrile (0.08% TFA) to yield 8.2 mg (0.008 mmol, 53%) of the title compound. MS (ESI) m/z 1025.0 [M+H]$^+$.

Example 35

4-(2-Amino-8-(3-(tert-butoxycarbonylamino)-propyl)-9H-purin-6-yloxymethyl)-benzyl-amine (53)

Trifluoroacetamide 11 (Example 23, 100 mg, 0.19 mmol) is dissolved in 2 mL methanol, and 2 mL methylamine (33% in ethanol) are added. The reaction mixture is stirred at 50° C. over night and all volatiles are removed in vacuo. The product is purified by flash column chromatography ($CH_2Cl_2$/MeOH 95:5 to 10:1) yielding 77 mg (0.017 mmol, 94%) of the title compound.

Example 36

N-[4-(2-Amino-8-(3-(tert-butoxycarbonylamino)-propyl)-9H-purin-6-yloxymethyl)-benzyl]-fluoresceine-5(6)-carboxamide (54)

Amine 53 (Example 35, 10 mg, 0.023 mmol) and 5(6)-carboxyfluoresceine succinimidyl ester (30, 11.4 mg, 0.023 mmol) are dissolved in 500 µL DMF with 10 µL TEA and stirred at room temperature over night, and the product is subsequently purified by reversed phase MPLC using a linear gradient from water to acetonitrile (0.08% TFA) to yield 13.4 mg (0.017 mmol, 73%) of the title compound. MS (ESI) m/z 766.0 [M+H]$^+$.

Example 37

N-[4-(2-Amino-8-(3-amino-propyl)-9H-purin-6-yloxymethyl)-benzyl]-fluoresceine-5(6)-carboxamide (55)

tert-Butoxycarbonylamide 54 (Example 36, 5 mg, 0.0062 mmol) is dissolved in 2 mL $CH_2Cl_2$/MeOH (1:1), and 1 mL of TFA is added. The mixture is stirred at room temperature for 4 h and all volatiles are removed in vacuo. The crude product is redissolved in 0.5 mL MeOH and purified by reverse phase MPLC using a linear gradient from water to acetonitrile (0.08% TFA) to yield 0.5 mg (0.0006 mmol, 10%) of the title compound. MS (ESI) m/z 686.2 [M+H]$^+$.

Example 38

Conjugate O$^6$-fluoresceine-C$^8$-bead (56)

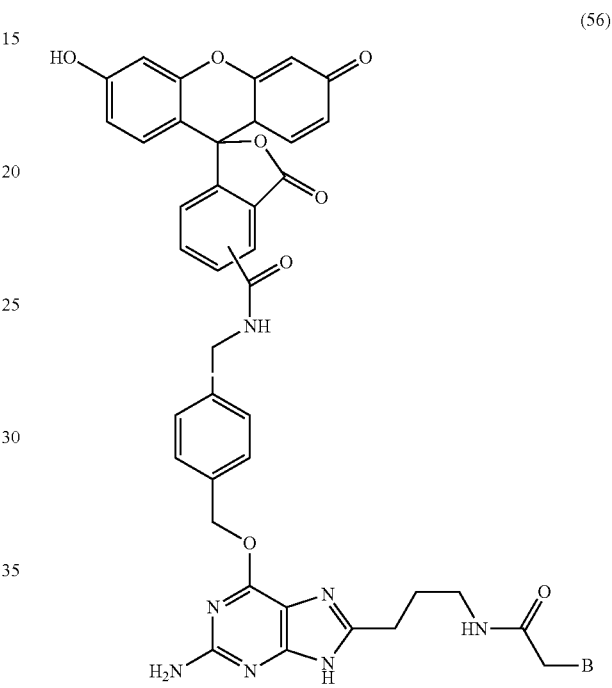

NHS-activated Sepharose™ is packed into a polypropylene column (HiTrap™, 1 mL column volume, Amersham Biosciences) and incubated with a solution of amine 55 (Example 37, 8 mM) in 0.5 M NaCl, pH 8.5, for 30 min. The column is washed first with 6 ml of Buffer A (0.5 M ethanolamine, 0.5 M NaCl, pH 8.3), followed by 6 ml of Buffer B (0.1 M acetic acid, 0.5 M NaCl, pH 4). To quench any remaining NHS esters the column is subsequently incubated with Buffer A for 30 min and then washed again with 6 ml of Buffer A, followed by 6 ml of Buffer B and then again 6 ml of Buffer A. The beads of formula 56 are now ready for use as a substrate for hAGT.

Example 39

N-[4-(2-Amino-8-(3-(tert-butoxycarbonylamino)-propyl)-9H-purin-6-yloxymethyl)-benzyl]-ATTO488-amide (57)

Amine 53 (Example 35, 2.5 mg, 0.08 mmol) and ATT0488-succinimidyl ester (28, 4 mg, 0.08 mmol) are dissolved in 500 µL DMF with 10 µL TEA and stirred at room temperature over night, and the product subsequently purified by reversed phase MPLC using a linear gradient from water to acetonitrile (0.08% TFA) to yield 13.4 mg (0.017 mmol, 73%) of the title compound.

Example 40

N-[4-(2-Amino-8-(3-amino-propyl)-9H-purin-6-yloxymethyl)-benzyl]-ATTO488-amide (58)

tert-Butoxycarbonylamide 57 (Example 39, 2 mg, 0.002 mmol) is dissolved in 1 mL $CH_2Cl_2$/MeOH (1:1), and 0.1 mL of TFA is added. The mixture is stirred at room temperature for 30 min and all volatiles are removed in vacuo. The crude product is redissolved in 0.5 mL MeOH and purified by reversed phase MPLC using a linear gradient from water to acetonitrile (0.08% TFA).

Example 41

N-[4-(2-Amino-8-(3-(maleimidoacetyl-amino)-propyl)-9H-purin-6-yloxymethyl)-benzyl]-ATTO488-amide (59)

Amine 58 (Example 40, 1 mg, 0.0011 mmol) and maleimidoacetic acid succinimidyl ester (1 mg, 0.0039 mmol) are dissolved in 100 µL DMF with 1 µL TEA and left at room temperature over night. The crude product is purified by reversed phase MPLC using a linear gradient from water to acetonitrile (0.08% TFA).

Example 42

Conjugate $O^6$-ATTO488-$C^8$-TyrArg$_9$Cys (60)

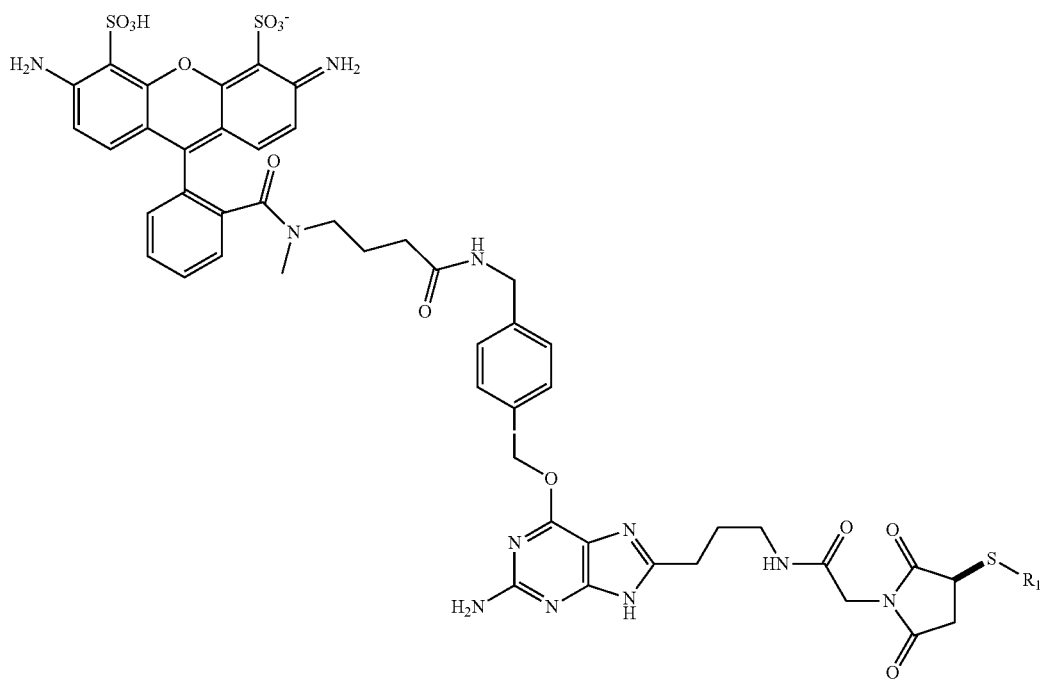

(60)

The maleimido fluorophore 59 (Example 41, 4 equiv.) in 50 mL acetonitrile is added to TyrArg$_9$Cys in 0.5 mL of deoxygenated MeOH and then shaken under $N_2$ for 2-4 h at room temperature. Ethyl ether (10 fold excess) is added to precipitate the product. Purification is carried out by reversed phase MPLC using a linear gradient from water to acetonitrile (0.08% TFA) with detection at the corresponding wavelength. The products are characterized by MALDI-TOF MS.

Example 43

2,5,6-Triamino-4-[4-(2,2,2-trifluoro-acetylamino-methyl)-benzyloxy]-pyrimidine (61)

2,6-Diamino-5-nitroso-4-[4-(2,2,2-trifluoro-acetylamino-methyl)-benzyloxy]-pyrimidine (1.22 g, 3.3 mmol) and triphenylphosphine (1.89 g, 7 mmol) in 20 mL o-xylene are heated to reflux for 1 h. After cooling to room temperature the solvent is removed in vacuo and the remaining residue redissolved in methanol. The residue is adsorbed on $SiO_2$ and purified by flash column chromatography ($CH_2Cl_2$/methanol 95:5 to 5:1) to yield the title compound.

Example 44

2-Amino-6-hydroxymethyl-4-[4-(2,2,2-trifluoro-acetylamino-methyl)-benzyloxy]-pteridine (62)

Pyrimidine 61 (Example 43, 5.0 g, 14.1 mmol) is dissolved in dimethylacetamide/water (1:1) with sodium ascorbate (2.85 g, 14.4 mmol). Dihydroxyacetone dimer (2.57 g, 14.3 mmol) is added and the reaction mixture is heated to 40° C. while air is bubbled into the reaction mixture. After 4 h the reaction mixture is poured into 250 mL of $H_2O$, and the formed solid collected by filtration. This solid is redissolved in $CH_2Cl_2$/MeOH (3:1, 500 mL), and dried over MgSO4. The crude product is adsorbed on $SiO_2$ and purified by flash column chromatography using $CH_2Cl_2$/MeOH (20:1).

Example 45

2-Amino-4-[4-(2,2,2-trifluoro-acetylamino-methyl)-benzyloxy]-pteridine-6-carboxylic acid (63)

Hydroxymethyl compound 62 (Example 44, 0.342 g, 0.84 mmol) is suspended in acetone/0.5 M phosphate buffer, pH 7 (1:1, 20 mL), and potassium permanganate (0.34 g, 2.18 mmol) is added in portions over 2 h. The reaction mixture is stirred at room temperature for 3 h, diluted with $H_2O$ (50 mL), and sodium sulfite is added until the permanganate is consumed, producing a brown-black precipitate, which is removed by filtration. The pH is adjusted to 2.5 by the addition of 2 M HCl, producing a yellow solid, which is collected by filtration. The solid is dissolved in $H_2O$ (50 mL) by adjusting the pH to 7.0 through the addition of 0.1 M NaOH until the pH remained constant for 30 min. The mixture is filtered, acidified again, and the crude product purified by reversed phase MPLC by using a linear gradient from water to acetonitrile (0.08% TFA).

Example 46

2-Amino-6-(3-(tert-butoxycarbonylamino)-propyl)-4-[4-(2,2,2-trifluoro-acetylamino-methyl)-benzyloxy]-pteridine (64)

Carboxylic acid 63 (Example 45, 0.10 g, 0.24 mmol) and PyBOP ((Benzotriazol-1-yloxy)-tripyrrolidinophosphonium hexafluorophosphate, 0.12 g, 0.24 mmol) are dissolved in 1 mL dry DMF and stirred at room temperature for 30 min. TEA (50 µL) and tert-butyl 2-aminoethylcarbamate (48 mg, 0.3 mmol) are added. The reaction mixture is stirred for additional 3 h and poured into 50 ml of water. The product is extracted with $CH_2Cl_2$, dried over $MgSO_4$ and purified via flash column chromatography using $CH_2Cl_2$/MeOH (20:1).

Example 47

Reaction rate of AGT mutants with $N^9$-cyclopentyl-$O^6$-(4-bromothiophen-2-yl)-guanine (18, CPTG)

A first AGT mutant Gly131Lys, Gly132Thr, Met134Leu, Arg135Ser, Asn157Gly, Ser159Glu is prepared by directed evolution. Two partially overlapping regions of the PGEG-hAGT gene, an AGT containing the mutations Asn157Gly, Ser159Glu (Juillerat et al., Chem Biol 10:313-317, 2003), are amplified with the suitable primers in separate reactions. The primers contain the nucleotide mixtures NNK (N=A, C, G or T; K=G or T) at positions corresponding to the codons 131, 132, 134, 135 of the hAGT gene. With respect to their partial complementarity, these two PCR fragments are assembled in a further PCR reaction, and amplified to give rise to full length genes randomised at codons 131, 132, 134, 135. These are cloned in fusion to the g3 protein of filamentous phage in the vector pAK100 via Sfi1 restriction sites. The resulting gene library is used for phage display.

Production of phages of this library is carried out in *E. coli* JM101 cells. An exponential culture is superinfected with helper phage and grown overnight at 24° C. The supernatant of this culture is incubated with 1 µM digoxigeninylated $O^6$-benzylguanine (substance 2 of Juillerat et al., Chem Biol 10:313-317, 2003) for 6 minutes. In subsequent selection rounds, the reaction time is decreased to 90 seconds and 45 seconds, respectively, and the concentration of substrate is decreased to 10 nM to increase selection pressure. Phages are purified from this reaction by precipitation with 4% PEG/3% NaCl. The phages carrying mutant AGT that is now covalently labeled with digoxigenin are isolated by incubation with magnetic beads coated with anti-digoxigenin antibodies (Roche Diagnostics), and used for re-infection of bacteria.

Selected AGT mutants are amplified and subsequently cloned between the BamH1 and EcoR1 sites of the expression vector pGEX-2T (Amersham). This allows the expression of the inserted gene as a C-terminal fusion to the GST protein, the gene of which is provided by the vector.

Protein expression from this vector is carried out in *E. coli* strain BL21. An exponentially growing culture is induced with 0.5 mM IPTG, and the expression is carried out for 3.5 h at 24° C.

Purification: The harvested cells are resuspended in a buffer containing 50 mM phosphate, 0.5 M NaCl, 1 mM DTT, supplemented with 1 mM PMSF and 2 µg/mL aprotinin, and disrupted by lysozyme and sonification. The cell debris are separated by centrifugation at 40000×g. The extract is applied to pre-equilibrated glutathione sepharose (Amersham) which is then washed with 20 bed volumes (50 mM phosphate, 0.5 M NaCl, 1 mM DTT). The mutated GST-AGT fusion protein is eluted with 10 mM reduced glutathione in 50 mM Tris.HCl pH 7.9. The purified protein is dialyzed against 50 mM HEPES pH 7.2; 1 mM DTT; 30% glycerol and then stored at −80° C.

A second AGT mutant ("AGTM") containing the mutations Cys62Ala, Gln115Ser, Gln116His, Lys125Ala, Ala127Thr, Arg128Ala, Gly131Lys, Gly132Thr, Met134Leu, Arg135Ser, Cys150Asn, Ser151Ile, Ser152Asn, Asn157Gly, Ser159Glu, and truncation at 182 is derived from the mentioned above AGT mutant by subsequent introduction of further mutations and a truncation after codon 182 into the mutant AGT gene. Subsequent PCR amplifications gives rise to the further mutated gene that is subcloned into pGEX2T as described for the first mutant. The GST-fusion protein is expressed and purified as well.

A third AGT mutant ("AGT21") related to AGTM and containing the mutations Cys62Ala, Gln115Ser, Gln116His, Lys125Ala, Ala127Thr, Arg128Ala, Arg135Ser, Cys150Asn, Ser151Ile, Ser152Asn, Asn157Gly, Ser159Glu, and truncation at 182 is prepared according to the same method.

A fourth AGT mutant ("AGT26") related to AGTM and containing the mutations Cys62Ala, Lys125Ala, Ala127Thr, Arg128Ala, Gly131Lys, Gly132Thr, Met134Leu, Arg135Ser, Cys150Ser, Asn157Gly, Ser159Glu, and truncation at 182 is also prepared according to the same method.

Figure 2:
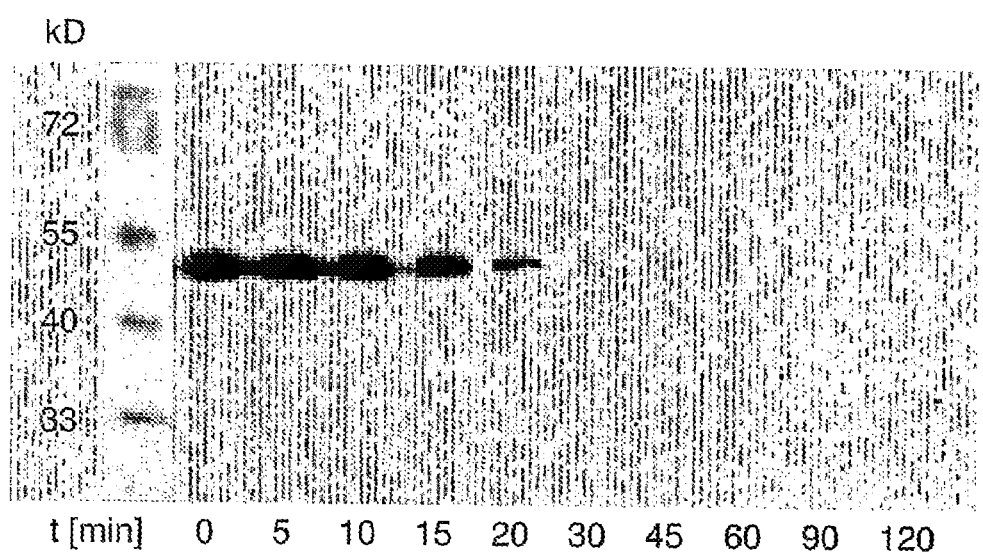
FIG. 2: Western blot for the AGTM-CPTG kinetic measurement: Intensity of the AGTM-BGBT complex detected with luminescent peroxidase substrate, see Example 8. Aliquots of mutant AGTM-6×His are incubated with 10fold excess of N[9]-cyclopentyl-O[6]-(4-bromothiophen-2-yl)-guanine (CPTG) in aqueous buffered solution. After a predetermined time, the reaction is quenched with a biotinylated O[6]-benzylguanine (BGBT, substance 3a of Juillerat et al., Chem Biol 10:313-317, 2003), which is supposed to react much faster with the protein, thus capturing unreacted AGTM. Proteins are then denatured with SDS and heat. Samples are subjected to SDS-PAGE and Western blot analysis. The intensity of the corresponding bands is detected by chemiluminescence stain.

AGTM (1 µM final concentration) is incubated with $N^9$-cyclopentyl-$O^6$-(4-bromothiophen-2-yl)-guanine (18, CPTG) (10 µM in 1% DMSO final concentration) in reaction buffer (50 mM HEPES, 1 mM DTT, 200 mg/mL BSA, pH 7.3) at 24° C. Samples are taken at defined times (5, 10, 15, 20, 30, 45, 60, 90, 120 min) and directly incubated with biotinylated $O^6$-benzylguanine (BGBT, substance 3a of Juillerat et al., Chem Biol 10:313-317, 2003, 10 µM final concentration) for 4 min. The reaction is quenched by addition of SDS-Laemmli buffer and heating for 2 min at 95° C. Samples are run on a 12% acrylamide gel and analysed by Western blotting. The result is shown in FIG. 2.

The second order rate constant is: $k_2=92.5$ [$s^{-1}$ $M^{-1}$]. This value is very slow compared to the activity of AGTM with BGBT ($k_2=~3,000$ [$s^{-1}$ $M^{-1}$]). The activity ratio of the two substrates BGBT/CPTG is at least 25.

Example 48

In vitro competitions between $N^9$-cyclopentyl-$O^6$-(4-bromothiophen-2-yl)-guanine (18, CPTG) and biotinylated $O^6$-benzylguanine (BGBT)

Mutant AGT (AGTM) and wild type human AGT (0.5 µM final concentration) are separately incubated with BGBT (0.5 µM final concentration) and different concentrations of CPTG (0, 0.5, 1, 5, 10 µM final concentrations) in reaction buffer (50 mM HEPES, 1 mM DTT, 200 mg/mL BSA, pH 7.3) for 45 min. The reaction is quenched by addition of 2×SDS buffer and placed 2 min at 95° C. Samples are run on a 12% acrylamide gel and analysed by Western blotting.

AGTM and wild type hAGT show significantly different reactivity toward CPTG in the presence of both compounds CPTG and BGBT. With a concentration of CPTG 20 times higher than BGBT, 95% of wild type AGT is quenched by CPTG after 45 minutes while 87% of the mutant AGTM is still active. As it is known that the rate constant of the reaction of wild type hAGT with BGBT is 400 $s^{-1}M^{-1}$, it can be assumed that the rate constant of wild type hAGT with CPTG is not significantly affected based on the known reactivity of hAGT with the sterically comparable $N^9$-desoxyribosyl-$O^6$-benzylguanine which gives a value of 340 $s^{-1}M^{-1}$ (Lodewijk et al., European Patent 704 445).

Figure 3:
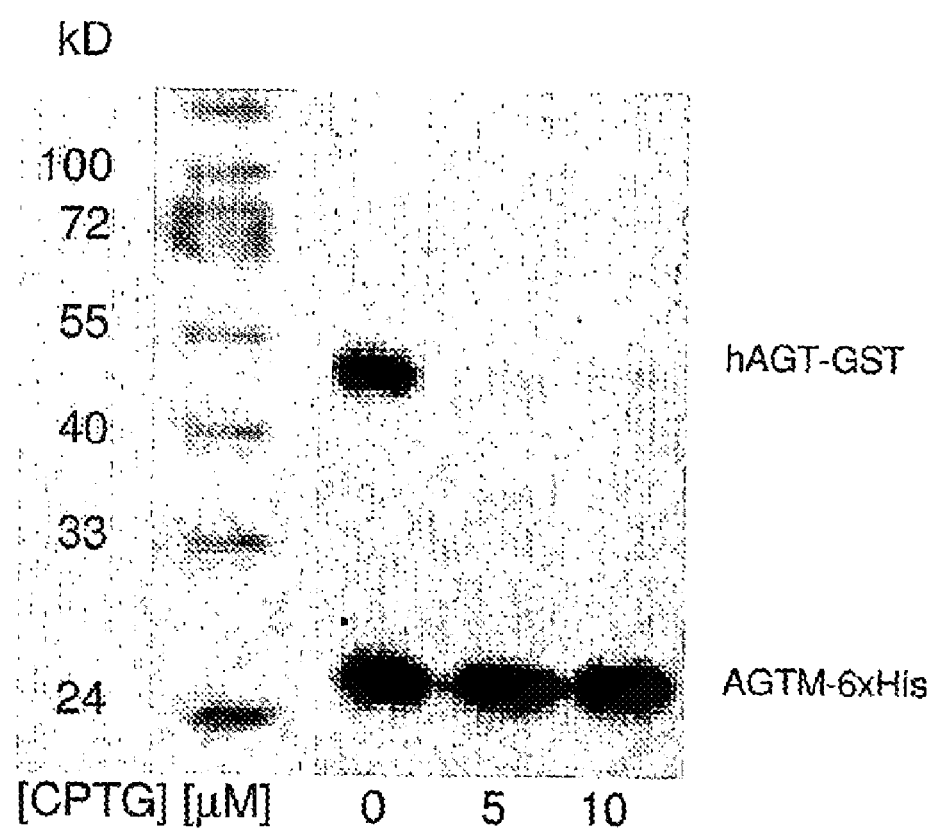
FIG. 3: Western blot of the reaction of the 2 proteins (AGTM-6×His at ~25 kDa, 0.2 μM, and wild type hAGT-GST fusion protein at ~50 kDa, 1.2 μM) with the two substrates N[9]-cyclopentyl-O[6]-(4-bromothiophen-2-yl)-guanine (CPTG, 0, 5 and 10 μM) and biotinylated O[6]-benzylguanine (BGBT, 5 μM), see Example 9. Detection of the AGTM-BGBT complex with luminescent peroxidase substrate is as described for FIG. 2.

A solution of both AGTM-6×His fusion protein (0.2 µM final concentration) and wild type hAGT-GST fusion protein (1.2 µM final concentration) in reaction buffer (50 mM HEPES, 1 mM DTT, 200 mg/mL BSA, pH 7.3) is incubated with BGBT (5 µM final concentration) and different concentrations of CPTG (0, 5, 10 µM final concentrations) for 30 min. The reaction is quenched by addition of 2×SDS buffer and placed 2 min at 95° C. Samples are run on a 12% acrylamide gel and analysed by Western blotting. The result is shown in FIG. 3.

In comparing the reaction of AGTM and wild type hAGT, a high specificity of CPTG toward hAGT is observed. At the same concentration (both substrates 5 µM final concentration), 95% of wild type AGT has reacted with CPTG versus only 5% of AGTM.

Example 49

Intracellular Competition of Two Different Agt Mutants in One Sample with Two Different Substrates The mutant AGTM (Example 47) is amplified with the suitable primers and cloned between the NheI and BglII sites of the vector pEGFP-Nuc. The yeast β-galactosidase gene is likewise amplified and subcloned into this vector via BglII/BamHI to result in a vector with an AGT-β-Gal fusion gene. The wild type hAGT gene is amplified and cloned via NheI/BglII into pEGFP-Nuc to result in an AGT-NLS3 fusion gene coding for the mutation Gly160Trp. After transient expression of both AGT mutants in parallel in CHO cells, the cells are incubated with 5 µM CPTG (18) for 10 min and subsequently with 5 µM of substance 4 of Juillerat et al., Chem Biol 10:313-317, 2003 ($O^6$-(4-(diacetyl-fluoresceine-carbonylaminomethyl)-benzyl)-guanine (BG-AcFL), for 20 min. The cells are washed and imaged according to standard procedures.

In CHO cells, the cytoplasmically localized AGT-β-galactosidase fusion protein is selectively fluorescence labeled by reaction with the fluorescent substrate BG-AcFL. No significant labeling of the other AGT fusion protein in the nucleus is observed. It is concluded that the AGT (Gly160Trp) efficiently reacts with CPTG (18) inside cells and therefore cannot be labeled with the fluorescent substrate afterwards. The mutant AGTM remains reactive to the fluorescent substrate after pre-incubation with CPTG inside cells and therefore does not react with CPTG in the first step.

Example 50

Fluorescence-Appearance Assay

Two aliquots of 100 µL hAGT-GST fusion protein in reaction buffer (50 mM Tris, 1 mM DTT, 1 mg/mL BSA, pH 8.0, final concentration of hAGT-GST: 1 µM) are placed in a black flat-bottomed microtiter plate. One aliquot serves as a control, which is quenched with benzylguanine (final concentration of 100 µM) for 40 min. Compound (7) in DMSO is added to both samples of hAGT-GST (final concentration 10 nM) and incubated at 25° C. for 1 hour. The fluorescence is read on a Victor² V plate reader (Perkin-Elmer) with the fluorescein-protocol. The fluorescence reading in the sample is at least twofold higher than in the control.

In a further assay, purified protein of AGT mutants AGTM and AGT21 (Example 47) at a protein concentration of 10 µM are incubated with 100 nM N-[4-(2-Amino-9-(3-QSY9-aminopropyl)-purin-6-yloxymethyl)-benzyl]-tetramethyl-rhodamine-5(6)-carboxamide (35, $N^9$-QSY9-BG-TMR, Example 19) in a buffer containing 100 mM NaCl, 50 mM Tris, pH 8.0, 0.1% Tween, 1 mM DTT, at room temperature. The fluorescence intensity (531 nm excitation/595 nm emission) is followed using a Victor2 microplate reader (Perkin Elmer). The mutant AGT21 shows significant reactivity towards $N^9$-QSY9-BG-TMR (compound 35) leading to an increase by about 80% of tetramethylrhodamine fluorescence over 1 hour at 25° C. In contrast the mutant AGTM shows less than five percent increase of tetramethylrhodamine fluorescence with $N^9$-QSY9-BG-TMR over 1 hour incubation at 25° C.

Similarly, AGTM and AGT21 are incubated with N-[4-(2-amino-8-(3-(4-[4-dimethylamino-phenyl]-azo-benzoyl)-aminopropyl)-9H-purin-6-yloxymethyl)-benzyl]-ATTO488-amide (45, $C^8$-Dabcyl-BG-Atto488, Example 28) and $O^6$-(4-(ATT0488-amidomethyl)-benzyl)-guanine (BG-Atto488, Atto-Tec Siegen, D, Prod Nr.: AD 488-2), and the fluorescence intensity measured at 490 nm (excitation) and 535 nm (emission). The mutant AGTM shows a 3 fold increased reactivity towards $C^8$-Dabcyl-BG-Atto488 compared to BG-Atto488. The mutant AGT21 shows a twofold increase in reactivity towards $C^8$-Dabcyl-BG-Atto488 compared to BG-Atto488.

Further reactivity comparisons gave the following results:

AGT21 reacts two times faster with compound 48 ($C^8$-QSY9-BG-TMR, Example 31) than with the compound unsubstituted at $C^8/N^9$ (BG-TMR, Molecular Probes product C300) and at least four times faster than with compound 35 ($N^9$-QSY9-BG-TMR, Example 19). AGT21 reacts two times faster with compound 45 ($C^8$-Dabcyl-BG-Atto488, Example 28) than with the compound unsubstituted at $C^8/N^9$ (BG-Atto488, Atto-Tec Siegen, D, Prod. No. AD 488-2) and at least four times faster than with compound 27 ($N^9$-Dabcyl-BG-Atto488, Example 14).

AGT21 reacts two times faster with compound 44 ($C^8$-Dabcyl-BG-FL, Example 27) than with the compound unsubstituted at $C^8/N^9$ (BG-FL, substance 5 of Juillerat et al., Chem Biol 10:313-317, 2003) and at least four times faster than with compound 29 ($N^9$-Dabcyl-BG-FL, Example 15).

AGTM reacts two times faster with compound 48 ($C^8$-QSY9-BG-TMR, Example 31) than with the compound unsubstituted at $C^8/N^9$ (BG-TMR) and at least ten times faster than with compound 35 ($N^9$-QSY9-BG-TMR, Example 19).

AGTM reacts three times faster with compound 45 ($C^8$-Dabcyl-BG-Atto488, Example 28) than with the compound unsubstituted at $C^8/N^8$ (BG-Atto488) and at least fifteen times faster than with compound 27 ($N^9$-Dabcyl-BG-Atto488, Example 14). AGTM reacts two times faster with compound 44 ($C^8$-Dabcyl-BG-FL, Example 27) than with the compound unsubstituted at $C^8/N^8$ (BG-FL) and at least ten times faster than with compound 29 ($N^9$-Dabcyl-BG-FL, Example 15).

Example 51

One-Pot Labeling and Separation Assay

50 μL hAGT-GFP fusion protein in reaction buffer (50 mM Tris, 1 mM DTT, 1 mg/mL BSA, pH 7.3, final concentration of hAGT-GFP: 5 μM) is incubated with substrate (9) (B=biotin, final concentration 10 μM) for 1 h. 150 μL streptavidin coated beads (Dynabeads M-280) are added and the incubation time and magnetic separation from the supernatant are done according to manufacturer's instruction for use. By measuring the GFP absorption at 488 nm, the amount of fusion protein in solution before and after the treatment with magnetic beads is determined. The loss of fusion protein is less than 30%. The labeling efficiency is determined by measuring the absorption of the ALEXA-dye at 594 nm in the supernatant after removal of the unreacted substrate. The labeling efficiency is at least 20%.

In other experiments, purified AGTM or AGT21 (Example 47) in a protein concentration of 5 μM are incubated with 10 μM N-[4-(2-amino-8-(3-(N-(+)-biotinyl-6-aminocaproyl)-aminopropyl)-9H-purin-6-yloxymethyl)-benzyl]-fluoresceine-5(6)-carboxamide (52, Example 34) in 50 μl buffer containing 100 mM NaCl, 50 mM Tris, pH 8.0, 0.1% Tween, 1 mM DTT at room temperature. After 1 hour, streptavidin coated magnetic beads (Magnabind Streptavidin, Pierce) with a capacity to bind at least 1 nmol biotin are added and the incubation time and magnetic separation from the supernatant containing fluorescein-labeled protein are done according to manufacturer's instructions for use. The amount of protein in solution before and after the treatment with magnetic beads is determined by Bradford assay. The loss of protein is less than 30%. The labeling efficiency is determined by measuring the fluorescence intensity using a Victor2 microplate reader (Perkin Elmer) at 490 nm excitation and 535 nm emission in the supernatant after removal of the unreacted substrate and released product by binding to the beads and magnetic separation. The labeling efficiency is at least 20%.

In a further experiment, wherein the substrate is pre-immobilized, streptavidin coated magnetic beads (Magnabind Streptavidin, Pierce) with a capacity to bind 2 pg biotin per ml are incubated with twofold excess of compound 52 (as above) in buffer containing 100 mM NaCl, 50 mM Tris, pH 8.0, 0.1% Tween at room temperature to immobilize the substrate to the beads. The incubation time and magnetic separation from the supernatant are done according to manufacturer's instructions for use. Unbound substrate is removed with buffer by 3 subsequent washing steps. AGTM at a protein concentration of 50 μM is incubated with these substrate-modified beads in 50 μl buffer containing 100 mM NaCl, 50 mM Tris, pH 8.0, 0.1% Tween, 1 mM DTT at room temperature. After 20 h, the beads are separated from the supernatant containing fluorescein-labeled protein. The amount of protein in solution before and after the treatment with magnetic beads is determined by Bradford assay. The loss of protein is less than 30%. The labeling efficiency is determined by measuring the fluorescence intensity as above and is at least 20%.

Example 52

Labeling Beads

Functionalized Sepharose beads 56 (Example 38) are equilibrated by washing with 5 ml of Buffer C (10 mM HEPES, pH 7.4, 150 mM NaCl, 0.05% Tween 20). To this suspension are added 100 μL of hAGT-GFP (final concentration of 50 μM) and incubated at 25° C. for 1 h. The sepharose beads are removed by centrifugation and the labeling efficiency is determined by measuring the absorption of the fluorescein at 488 nm in the supernatant. The labeling efficiency is at least 20%. By measuring the GFP absorption at 488 nm, the amount of fusion protein in solution before and after the treatment with modified sepharose beads is determined. The loss of fusion protein is less than 30%.

In an alternative experiment compound 56 is prepared with Sepharose4FastFlow (carboxylic groups activated as NHS-ester, Amersham Prod No. 17-0906-01) according to the instructions given by the manufacturer. The resin material is washed until no fluorescence can be detected in the washing solution and is stored at 4° C. in the dark. The buffer used for all following steps is 150 mM NaCl with 50 mM Tris, at pH 8.0 plus 1 mM DTT. For each experiment 200 μL of the modified resin are packed into a Bio-Rad Micro Biospin spin column and centrifuged for 2 min at 1000×g according to the manufacturers instructions. The run through is discarded. Afterwards 100 μL non labeled AGTM at 50 μM concentration are added and left for 1 hour in the dark at 25° C. As a control experiment 100 μL of 50 μM AGTM preblocked for 30 min with 100 μM $O^6$-benzylguanine are used. Afterwards the columns are centrifuged for 2 min at 1000×g and washed four times, each time by addition of 200 μL buffer. The final volume is adjusted to 1 mL. The protein content is determined by the BCA assay (Pierce BCA protein assay kit—Prod. Nr. 23225, Perbio Science, Switzerland). The values found are at least 80% of the expected 5 μM concentration. The fluorescence of all solutions is determined after dilution 1:50 with 100 mM $Na_2CO_3$ buffer adjusted to pH 9. A black 96 well plate (Costar) is equipped with 200 μL of each sample. The fluorescence in the fluorescein range of the test sample is read by a Victor 2 plate reader (fluorescein filter set). The fluorescence found for the test sample is at least 5 times the fluorescence found for the control experiment.

Example 53

Cell permeability of conjugate $O^6$-ATT0488-$C^8$-TyrArg$_9$ Cys (60)

A vector for a fusion of AGT26 and the CaaX-farnesylation signal is transfected into CHO cells deficient in endogenous wildtype AGT. Stable transfectants are selected under geneticine treatment. For that purpose the gene of AGT26 is cloned into pCMV-Script (Stratagene) followed on its C-terminus by the CaaX-box sequence encoded in the pECP-F (Clontech). The final protein sequence (position 690-1271) yields a single polypeptide with 194 amino acids. In the stably transfected cell line this polypeptide leads to an AGT fusion protein localized to the inner surface of the cell membrane. This AGT fusion protein yields a clear signal at the cell membrane when these cells are labeled for 30 min with 5 μM $O^6$-tetramethylrhodamine-benzylguanine (BG-TMR, synthesized from TMR-NHS-ester, Molecular Probes product C300), followed by two exchanges of culture medium, then a 30 min resting period and a further exchange of the culture medium. All imaging is done with an inverted Zeiss fluorescence microscope Axiovert 40 CFL with filter sets for tetramethylrhodamine and for fluorescein. Upon incubation with 5 μM $O^6$-Atto488-benzylguanine (BG-Atto488, Atto-Tec Siegen, D, Prod. No. AD 488-2) following the same sequence of steps no significant labeling of the cells is observed. This indicates that the bis-sulfonated Atto488 derivative has only very low cell membrane permeability. When conjugate $O^6$-ATT0488-$C^8$-TyrArg$_9$Cys (60, Example 42) is used at a concentration of 5 μM under the same conditions, significant intracellular staining is observed with a dominant labeling of the cell membrane. This indicates that the introduction of the poly-arginine linker leads to increased permeability of the otherwise not cell permeable benzylguanine derivative.

The invention claimed is:

1. A compound of formula (1)

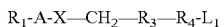

wherein
the group $R_1$-A is a purine radical of formula (2)

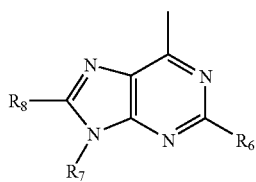

X is oxygen;
$R_1$ is a group —$R_2$-$L_2$;
$R_2$ and $R_4$ are, independently of each other, a straight or branched chain alkylene group or polyvalent branched chain alkyl group with 1 to 300 carbon atoms, optionally substituted by a lower alkyl, lower alkoxy, lower acyloxy or halogen wherein optionally
  (a) one or more carbon atoms are replaced by oxygen;
  (b) one or more carbon atoms are replaced by nitrogen carrying a hydrogen atom, and the adjacent carbon atom is substituted by oxo;
  (c) one or more carbon atoms are replaced by oxygen, and the adjacent carbon atom is substituted by oxo;
  (d) the bond between two adjacent carbon atoms is a double or a triple bond;
  (e) one or more carbon atoms are replaced by a phenylene, a saturated or unsaturated cycloalkylene, a saturated or unsaturated bicycloalkylene, a divalent heteroaromatic or a divalent saturated or unsaturated heterocyclyl group;
  (f) two adjacent carbon atoms are replaced by a disulfide linkage;
  or a combination of two or more alkylene and/or modified alkylene groups as defined under (a) to (f) hereinbefore;
$R_3$ is an aromatic or a heteroaromatic group, or an optionally substituted 1-alkylene, 1-alkenylene, 1-cycloalkenylene, or an unsaturated heterocyclyl group with the double bond connected to $CH_2$;

$R_6$ is hydrogen, hydroxy or unsubstituted amino; one of $R_7$ or $R_8$ is $R_1$ and the other one is hydrogen; and
$L_1$ and $L_2$ are the same or different labels and each is selected from the group consisting of a fluorophore or a chromophore, a magnetic probe, a contrast reagent, a radioactive moiety, avidin, streptavidin, biotin, a moiety which is capable of crosslinking to other molecules selected from a maleimide, an activated carboxy group, an azide and a benzophenone; a tethered metal-chelate which is capable of generating hydroxyl radicals upon exposure to $H_2O_2$, ascorbate, malachite green, a solid support, a lipid, methotrexate, a linear poly(arginine) of D- and/or L-arginine with 6-15 arginine residues, oligomers of 6-50 subunits wherein at least one subunit has an attached guanidine group or a peptide having an RKKRRQRRR amino acid sequence (SEQ ID NO: 1); or
$L_1$ is a bond connecting $R_4$ to A forming a cyclic substrate; a further group —$R_3$—$CH_2$—X-A-$R_1$; or a nucleic acid or a derivative thereof capable of undergoing base-pairing with its complementary strand; or
if $R_7$ is a hydrogen then $L_2$ is capable of undergoing base-pairing with its complementary strand where $L_2$ is a nucleic acid.

2. The compound according to claim 1, wherein $R_3$ is phenylene, an unsubstituted or substituted mono- or bicyclic divalent heteroaryl group of 5 or 6 rings atoms comprising zero, one, two, three or four ring nitrogen atoms and zero or one oxygen atom and zero or one sulfur atom, with the proviso that at least one ring carbon atom is replaced by a nitrogen, oxygen or sulfur atom, 1-alkylene, 1-alkenylene, 1-cyclohexenylene with 3 to 7 carbon atoms, wherein the double or triple bond is connected to $CH_2$, or an optionally substituted unsaturated divalent heterocyclyl group with 3 to 12 atoms and 1 to 5 heteroatoms selected from nitrogen, oxygen and sulfur, and a double bond in the position connecting the heterocyclyl group to $CH_2$.

3. The compound according to claim 1, wherein $R_3$ is phenylene.

4. The compound according to claim 1, wherein $R_3$ is thienylene.

5. The compound according to claim 1, wherein $R_6$ is unsubstituted amino, $R_7$ is $R_1$, and $R_8$ is hydrogen.

6. The compound according to claim 1, wherein $L_2$ is a fluorophore or a chromophore.

7. The compound according to claim 1, wherein $L_1$ is a fluorophore or a chromophore and $L_2$ is a fluorophore or a chromophore.

8. The compound according to claim 7, wherein $L_1$ is a fluorescence donor and $L_2$ is a fluorescence quencher or $L_1$ is a fluorescence quencher and $L_2$ is a fluorescence donor.

9. The compound according to claim 7, wherein $L_1$ and $L_2$ constitute a FRET pair.

10. The compound according to claim 1, wherein $R_6$ is unsubstituted amino, $R_7$ is hydrogen, and $R_8$ is $R_1$.

11. The compound according to claim 1, wherein $R_6$ is unsubstituted amino, $R_7$ is hydrogen, and $R_8$ is a group —$R_2$-$L_2$.

12. The compound according to claim 11, wherein $L_2$ is a fluorophore or a chromophore.

13. The compound according to claim 12, wherein $L_1$ is a fluorophore or a chromophore.

14. The compound according to claim 13, wherein $L_1$ and $L_2$ constitute a fluorescence donor or a fluorescence quencher.

15. The compound according to claim 14, wherein $L_1$ and $L_2$ constitute a donor or an acceptor in a FRET pair.

16. The compound according to claim 11, wherein $L_2$ is avidin, streptavidin or biotin.

17. The compound according to claim 11, wherein $L_2$ is a moiety covalently attached to a solid support.

18. The compound according to claim 11, wherein $L_2$ is a linear poly(arginine) of D- and/or L-arginine with 6-15 arginine residues, an oligomer of 6-50 subunits wherein at least one subunit has an attached guanidine group or a peptide having an RKKRRQRRR amino acid sequence (SEQ ID NO: 1).

19. A method for detecting a protein of interest, wherein the protein of interest is fused to a mutant of a human AGT, the method comprising:
  (a) contacting the AGT fusion protein with a compound of formula (1) according to claim 1; and
  (b) detecting the AGT fusion protein using label $L_1$ and/or $L_2$ in a system designed for recognizing and/or handling the label.

20. The method according to claim 19, wherein in the compound of formula (1) $L_2$ is a solid support, and the AGT fusion protein contacted with the compound of formula (1) is separated from the compound of formula (1) by filtration or centrifugation or separation of magnetic beads.

21. The method according to claim 19, wherein in the compound of formula (1) $L_1$ is one member and $L_2$ the other member of two interacting chromophores or fluorophores, wherein energy can be transferred non-radiatively through dynamic or static quenching, and the AGT fusion protein is detected by fluorescence.

22. The method according to claim 19 for detecting a protein of interest, wherein the protein of interest is fused with a mutant of a human AGT, comprising:
  (a) contacting the mutant of the human AGT fusion protein with a mixture of
    (i) a compound of formula (1) wherein $R_1$ additionally comprises $R_5$, wherein $R_5$ is a substituted or unsubstituted cycloalkyl, cycloalkenyl or heterocyclyl group which does not react with the mutant AGT; and
    (ii) another compound of formula (1), which reacts with the mutant AGT fusion protein; and
  (b) detecting the mutant AGT fusion protein using the label in a system designed for recognizing and/or handling the label.

\* \* \* \* \*